(12) United States Patent
Rohan et al.

(10) Patent No.: US 11,672,757 B2
(45) Date of Patent: Jun. 13, 2023

(54) HOT MELT EXTRUSION FOR PHARMACEUTICAL VAGINAL FILM PRODUCTS

(71) Applicant: UNIVERSITY OF PITTSBURGH-OF THE COMMONWEALTH SYSTEM OF HIGHER EDUCATION, Pittsburgh, PA (US)

(72) Inventors: Lisa Cencia Rohan, Pittsburgh, PA (US); Galit Regev, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 312 days.

(21) Appl. No.: 16/626,382

(22) PCT Filed: Jun. 28, 2018

(86) PCT No.: PCT/US2018/040012
§ 371 (c)(1),
(2) Date: Dec. 24, 2019

(87) PCT Pub. No.: WO2019/006122
PCT Pub. Date: Jan. 3, 2019

(65) Prior Publication Data
US 2021/0145734 A1 May 20, 2021

Related U.S. Application Data

(60) Provisional application No. 62/526,021, filed on Jun. 28, 2017.

(51) Int. Cl.
| | | |
|---|---|---|
| A61K 9/00 | (2006.01) | |
| A61P 31/04 | (2006.01) | |
| A61K 9/70 | (2006.01) | |
| A61K 31/4164 | (2006.01) | |
| A61K 31/505 | (2006.01) | |
| A61K 31/567 | (2006.01) | |
| A61K 35/747 | (2015.01) | |
| A61K 38/16 | (2006.01) | |
| A61K 47/10 | (2017.01) | |
| A61K 47/38 | (2006.01) | |

(52) U.S. Cl.
CPC .......... *A61K 9/0036* (2013.01); *A61K 9/7007* (2013.01); *A61K 31/4164* (2013.01); *A61K 31/505* (2013.01); *A61K 31/567* (2013.01); *A61K 35/747* (2013.01); *A61K 38/16* (2013.01); *A61K 47/10* (2013.01); *A61K 47/38* (2013.01); *A61P 31/04* (2018.01)

(58) Field of Classification Search
CPC .......... A61K 9/0036; A61K 9/7007; A61K 31/4164; A61K 31/505; A61K 31/567; A61K 35/747; A61K 38/16; A61K 47/10; A61K 47/38; A61P 31/04
See application file for complete search history.

(56) References Cited

U.S. PATENT DOCUMENTS

| | | |
|---|---|---|
| 4,713,243 A | 12/1987 | Schiraldi |
| 4,764,378 A | 6/1988 | Keith et al. |
| RE33,093 E | 10/1989 | Schiraldi et al. |
| 6,375,963 B1 | 4/2002 | Repka et al. |
| 2001/0006677 A1 | 7/2001 | McGinity |
| 2006/0135458 A1* | 6/2006 | Vaillant ............... A61P 31/16 536/23.1 |
| 2008/0229609 A1 | 9/2008 | Bronshtein |
| 2010/0092545 A1 | 4/2010 | Yang et al. |
| 2010/0326454 A1 | 12/2010 | Fuisz |
| 2011/0236666 A1 | 9/2011 | Hall et al. |
| 2012/0308635 A1 | 12/2012 | Bruce et al. |
| 2013/0011462 A1 | 1/2013 | Bruce et al. |
| 2014/0128456 A1* | 5/2014 | Bandholtz ............ A61P 25/00 514/44 R |
| 2014/0209100 A1 | 7/2014 | Kiser et al. |
| 2017/0028074 A1 | 2/2017 | Payne et al. |

OTHER PUBLICATIONS

International Preliminary Report on Patentability issued for Application No. PCT/US2018/040014, dated Jan. 9, 2020.
Aharoni, S.M., Increased glass transition temperature in motionally constrained semicrystalline polymers. Polymers for Advanced Technologies, 1998. 9(3): p. 169-201.
Aitken-Nichol, C., F. Zhang, and J.W. McGinity, Hot melt extrusion of acrylic films. Pharmaceutical Research, 1996. 13(5): p. 804-808.
Akil, A., et al., Formulation and characterization of polymeric films containing combinations of antiretrovirals (ARVs) for HIV prevention. Pharm Res, 2015. 32(2): p. 458-68.
Akil, A., M. A. Parniak, C. S. Dezzuitti, B. J. Moncla, M. R. Cost, M. Li and L. C. Rohan (2011). "Development and Characterization of a Vaginal Film Containing Dapivirine, a Non-nucleoside Reverse Transcriptase Inhibitor (NNRTI), for prevention of HIV-1 sexual transmission." Drug Deliv Transl Res 1(3): 209-222.
Alexandre, K., et al. Abstract P15.04 on p. A-78 "Griffithsin, Cyanovirin-N and Scytovirin Inhibit HIV-1 Binding and Transfer via the DC-SIGN Receptor." in Aids Research and Human Retroviruses. 2011. Mary Ann Liebert Inc 140 Huguenot Street, 3rd Fl, New Rochelle, Ny 10801 USA.
Amsel, R., et al., Nonspecific vaginitis. Diagnostic criteria and microbial and epidemiologic associations. Am J Med, 1983. 74(1): p. 14-22.

(Continued)

*Primary Examiner* — Robert A Wax
*Assistant Examiner* — Olga V. Tcherkasskaya
(74) *Attorney, Agent, or Firm* — Meunier Carlin & Curfman LLC

(57) ABSTRACT

Hot melt extrusion is disclosed as a process for forming vaginal drug delivery films. The methods involve extruding a composition comprising one or more active pharmaceutical ingredients and one or more polymer carriers at an elevated temperature through a die to thereby provide the film. Films prepared by hot melt extrusion are also described.

24 Claims, 6 Drawing Sheets

(56) References Cited

OTHER PUBLICATIONS

Austin, M., et al., Microbiologic response to treatment of bacterial vaginosis with topical clindamycin or metronidazole. Journal of clinical microbiology, 2005. 43(9): p. 4492-4497.
Baeten, J.M., et al., Use of a vaginal ring containing dapivirine for HIV-1 prevention in women. New England Journal of Medicine, 2016, 12 pages.
Barnhart, K.T., et al., Baseline dimensions of the human vagina. Hum Reprod, 2006. 21(6): p. 1618-22.
Bradshaw, C.S., et al., High recurrence rates of bacterial vaginosis over the course of 12 months after oral metronidazole therapy and factors associated with recurrence. J Infect Dis, 2006. 193(11): p. 1478-86.
Bradshaw, C.S., et al., Recurrence of bacterial vaginosis is significantly associated with posttreatment sexual activities and hormonal contraceptive use. Clinical infectious diseases, 2013. 56(6): p. 777-786.
Breitenbach, J., Melt extrusion: from process to drug delivery technology. Eur J Pharm Biopharm, 2002. 54(2): p. 107-17.
Brunelli, R., et al., Globular structure of human ovulatory cervical mucus. The FASEB journal, 2007. 21(14): p. 3872-3876.
Bunge, K.E., et al., A Phase 1 Trial to Assess the Safety, Acceptability, Pharmacokinetics, and Pharmacodynamics of a Novel Dapivirine Vaginal Film. J Acquir Immune Defic Syndr, 2016. 71(5): p. 498-505.
Chavoustie, S.E., et al., Metronidazole vaginal gel 1.3% in the treatment of bacterial vaginosis: A dose-ranging study. Journal of lower genital tract disease, 2015. 19(2): p. 129-134.
Clark, M.R., et al., A hot-melt extruded intravaginal ring for the sustained delivery of the antiretroviral microbicide UC781. Journal of pharmaceutical sciences, 2012. 101(2): p. 576-587.
Consultation, F.a.A.O.a.W.H.O.E., Health and Nutritional Properties of Probiotics in Food including Powder Milk with Live Lactic Acid Bacteria. Food and Agriculture Organization of the United Nations and World Health Organization, 2001: p. 1-34.
Crowley, M.M., et al., Pharmaceutical applications of hot-melt extrusion: part I. Drug Dev Ind Pharm, 2007. 33(9): p. 909-26.
Crowley, M.M., et al., Physicochemical properties and mechanism of drug release from ethyl cellulose matrix tablets prepared by direct compression and hot-melt extrusion. International journal of pharmaceutics, 2004. 269(2): p. 509-522.
Crowley, M.M., et al., Stability of polyethylene oxide in matrix tablets prepared by hot-melt extrusion. Biomaterials, 2002. 23(21): p. 4241-4248.
D'Souza, A Review of In Vitro Drug Release Test Methods for Nano-Sized Dosage Forms. Advances in Pharmaceutics, 2014. 2014: p. 12.
Daniels, K., W.D. Mosher, and J. Jones, Contraceptive methods women have ever used: United States, 1982-2010. National health statistics reports, 2013. 62(20): p. 2013.
D'Cruz, O.J. and F.M. Uckun, Dawn of non-nucleoside inhibitor-based anti-HIV microbicides. Journal of Antimicrobial Chemotherapy, 2006. 57(3): p. 411-423.
Deng, W., et al., Stabilization of fenofibrate in low molecular weight hydroxypropylcellulose matrices produced by hot-melt extrusion. Drug Dev Ind Pharm, 2013. 39(2): p. 290-8.
Deshpande, A.A., C.T. Rhodes, and M. Danish, Intravaginal drug delivery. Drug Development and Industrial Pharmacy, 1992. 18(11-12): p. 1225-1279.
Dhawan, S., et al., Application of poly (ethylene oxide) in drug delivery systems. Part II. Pharm. Tech., 2005, 29:82-96.
Elias, C. and C. Coggins, Acceptability research on female-controlled barrier methods to prevent heterosexual transmission of HIV: Where have we been? Where are we going? J Womens Health Gend Based Med, 2001. 10(2): p. 163-73.
Emau, P., et al., Griffithsin, a potent HIV entry inhibitor, is an excellent candidate for anti-HIV microbicide. Journal of medical primatology, 2007. 36(4-5): p. 244-253.
Eschenbach, D., Treatment of pelvic inflammatory disease. Clin Infect Dis, 2007. 44(7): p. 961-3.
Eschenbach, D.A., Bacterial vaginosis: resistance, recurrence, and/or reinfection? Clin Infect Dis, 2007. 44(2): p. 220-1.
Eschenbach, D.A., et al., Prevalence of hydrogen peroxide-producing *Lactobacillus* species in normal women and women with bacterial vaginosis. J Clin Microbiol, 1989. 27(2): p. 251-6.
Evans, A.B., et al., Drug-drug Interaction Studies Investigating the Impact of Levonorgestrel on Antiviral Potency of Dapivirine. AIDS research and human retroviruses, 2014. 30(S1): p. A137-A137.
Falagas, M., G.I. Betsi, and S. Athanasiou, Probiotics for the treatment of women with bacterial vaginosis. Clin Microbiol Infect, 2007. 13(7): p. 657-64.
Ferguson, L.M. and L.C. Rohan, The importance of the vaginal delivery route for antiretrovirals in HIV prevention. Ther Deliv, 2011. 2(12): p. 1535-50.
Fethers, K.A., et al., Sexual risk factors and bacterial vaginosis: a systematic review and meta-analysis. Clinical Infectious Diseases, 2008. 47(11): p. 1426-1435.
Fletcher, P., et al., Inhibition of human immunodeficiency virus type 1 infection by the candidate microbicide dapivirine, a non-nucleoside reverse transcriptase inhibitor. Antimicrobial agents and chemotherapy, 2009. 53(2): p. 487-495.
Follonier, N., E. Doelker, and E.T. Cole, Evaluation of hot-melt extrusion as a new technique for the production of polymer-based pellets for sustained release capsules containing high loadings of freely soluble drugs. Drug Development and Industrial Pharmacy, 1994. 20(8): p. 1323-1339.
Follonier, N., E. Doelker, and E.T. Cole, Various ways of modulating the release of diltiazem hydrochloride from hot-melt extruded sustained release pellets prepared using polymeric materials. Journal of Controlled Release, 1995. 36(3): p. 243-250.
Friend, D.R. and G.F. Doncel, Combining prevention of HIV-1, other sexually transmitted infections and unintended pregnancies: Development of dual-protection technologies. Antiviral Res, 2010. 88 Suppl 1: p. S47-54.
Friend, D.R., et al., Multipurpose prevention technologies: products in development. Antiviral Res, 2013. 100 Suppl: p. S39-47.
Garg, S., et al., Advances in development, scale-up and manufacturing of microbicide gels, films, and tablets. Antiviral Res, 2010. 88 Suppl 1: p. S19-29.
Garg, S., et al., Development and characterization of bioadhesive vaginal films of sodium polystyrene sulfonate (PSS), a novel contraceptive antimicrobial agent. Pharm Res, 2005. 22(4): p. 584-95.
Gutierrez-Rocca, J.C. and J.W. Mcginity, Influence of aging on the physical-mechanical properties of acrylic resin films cast from aqueous dispersions and organic solutions. Drug Development and Industrial Pharmacy, 1993. 19(3): p. 315-332.
Hallen, A., C. Jarstrand, and C. Pahlson, Treatment of bacterial vaginosis with lactobacilli. Sex Transm Dis, 1992. 19(3): p. 146-8.
Ham, A.S., et al., Vaginal film drug delivery of the pyrimidinedione IQP-0528 for the prevention of HIV infection. Pharmaceutical research, 2012. 29(7): p. 1897-1907.
Hawes, S.E., et al., Hydrogen peroxide-producing lactobacilli and acquisition of vaginal infections. J Infect Dis, 1996. 174(5): p. 1058-63.
Hussain, A. and F. Ahsan, The vagina as a route for systemic drug delivery. J Control Release, 2005. 103(2): p. 301-13.
Jani, R. and D. Patel, Hot melt extrusion: An industrially feasible approach for casting orodispersible film, asian journal of pharmaceutical sciences, 2015. 10(4): p. 292-305.
Johnson, T.J., et al., Segmented polyurethane intravaginal rings for the sustained combined delivery of antiretroviral agents dapivirine and tenofovir. European Journal of Pharmaceutical Sciences, 2010. 39(4): p. 203-212.
Karim, S.S.A., et al., Drug concentrations after topical and oral antiretroviral pre-exposure prophylaxis: implications for HIV prevention in women. Lancet, 2011. 378(9787): p. 279.
Klein, C.E., et al., The tablet formulation of lopinavir/ritonavir provides similar bioavailability to the soft-gelatin capsule formulation with less pharmacokinetic variability and diminished food effect. JAIDS Journal of Acquired Immune Deficiency Syndromes, 2007. 44(4): p. 401-410.

(56) References Cited

OTHER PUBLICATIONS

Krohn, M.A., S.L. Hillier, and D.A. Eschenbach, Comparison of methods for diagnosing bacterial vaginosis among pregnant women. J Clin Microbiol, 1989. 27(6): p. 1266-71.
Ma, B., L.J. Forney, and J. Ravel, Vaginal microbiome: rethinking health and disease. Annu Rev Microbiol, 2012. 66: p. 371-89.
Machado, R.M., et al., Vaginal Films for Drug Delivery. Journal of Pharmaceutical Sciences, 2013. 102(7): p. 2069-2081.
Macht, D.I., On the absorption of drugs and poisons through the vagina. Journal of Pharmacology and Experimental Therapeutics, 1918. 10(7): p. 509-522.
Maniruzzaman, M., 3 Co-extrusion as a Novel Approach in Continuous Manufacturing Compliance. Practical Guide to Hot-Melt Extrusion. 2015. 10 pages.
Maniruzzaman, M., et al., A review of hot-melt extrusion: process technology to pharmaceutical products. ISRN Pharm, 2012. 2012: p. 436763.
Marcone, V., E. Calzolari, and M. Bertini, Effectiveness of vaginal administration of Lactobacillus rhamnosus following conventional metronidazole therapy: how to lower the rate of bacterial vaginosis recurrences. New Microbiol, 2008. 31(3): p. 429-33.
Martin, C., Twin screw extrusion for pharmaceutical processes, in Melt Extrusion. 2013, Springer, p. 47-79.
Martin, H.L., et al., Vaginal lactobacilli, microbial flora, and risk of human immunodeficiency virus type 1 and sexually transmitted disease acquisition. Journal of Infectious Diseases, 1999. 180(6): p. 1863-1868.
Mastromarino, P., et al., Characterization and selection of vaginal Lactobacillus strains for the preparation of vaginal tablets. J Appl Microbiol, 2002. 93(5): p. 884-93.
Mauck, C.K., et al., A phase I comparative study of contraceptive vaginal films containing benzalkonium chloride and nonoxynol-9: Postcoital testing and colposcopy. Contraception, 1997. 56(2): p. 89-96.
Mauck, C.K., et al., A phase I comparative study of three contraceptive vaginal films containing nonoxynol-9. Postcoital testing and colposcopy. Contraception, 1997. 56(2): p. 97-102.
Meuleman, P., et al., Griffithsin has antiviral activity against hepatitis C virus. Antimicrobial agents and chemotherapy, 2011. 55(11): p. 5159-5167.
Mishra, R., P. Joshi, and T. Mehta, Formulation, development and characterization of mucoadhesive film for treatment of vaginal candidiasis. Int J Pharm Investig, 2016. 6(1): p. 47-55.
Ndesendo, V.M., et al., A review of current intravaginal drug delivery approaches employed for the prophylaxis of HIV/AIDS and prevention of sexually transmitted infections. AAPS PharmSciTech, 2008. 9(2): p. 505-20.
Nel, A., et al., A safety and pharmacokinetic trial assessing delivery of dapivirine from a vaginal ring in healthy women. AIDS, 2014. 28(10): p. 1479-1487.
Nel, A.M., et al., Acceptability of vaginal film, soft-gel capsule, and tablet as potential microbicide delivery methods among African women. J Womens Health (Larchmt), 2011. 20(8): p. 1207-14.
Nel, A.M., et al., Safety, tolerability, and systemic absorption of dapivirine vaginal microbicide gel in healthy, HIV-negative women. Aids, 2009. 23(12): p. 1531-1538.
Nixon, B., et al., Griffithsin protects mice from genital herpes by preventing cell-to-cell spread. Journal of virology, 2013. 87(11): p. 6257-6269.
Novak, A., et al., The combined contraceptive vaginal ring, NuvaRing®: an international study of user acceptability. Contraception, 2003. 67(3): p. 187-194.
Nugent, R.P., M.A. Krohn, and S.L. Hillier, Reliability of diagnosing bacterial vaginosis is improved by a standardized method of gram stain interpretation. J Clin Microbiol, 1991. 29(2): p. 297-301.
Oduyebo, O.O., R.I. Anorlu, and F.T. Ogunsola, The effects of antimicrobial therapy on bacterial vaginosis in non-pregnant women. Cochrane Database Syst Rev, 2009(3): p. CD006055.
O'Hanlon, D.E., T.R. Moench, and R.A. Cone, In vaginal fluid, bacteria associated with bacterial vaginosis can be suppressed with lactic acid but not hydrogen peroxide. BMC Infect Dis, 2011. 11: p. 200.
O'Keefe, B.R., et al., Broad-spectrum in vitro activity and in vivo efficacy of the antiviral protein griffithsin against emerging viruses of the family Coronaviridae. Journal of virology, 2010. 84(5): p. 2511-2521.
Owen, D.H. and D.F. Katz, A vaginal fluid simulant. Contraception, 1999. 59(2): p. 91-5.
Pendergrass, P.B., et al., Comparison of vaginal shapes in Afro-American, Caucasian and hispanic women as seen with vinyl polysiloxane casting. Gynecol Obstet Invest, 2000. 50(1): p. 54-9.
Pendergrass, P.B., et al., The shape and dimensions of the human vagina as seen in three-dimensional vinyl polysiloxane casts. Gynecol Obstet Invest, 1996. 42(3): p. 178-82.
Pendergrass, P.B., M.W. Belovicz, and C.A. Reeves, Surface area of the human vagina as measured from vinyl poly siloxane casts. Gynecol Obstet Invest, 2003. 55(2): p. 110-3.
Prodduturi, S., et al., Solid-state stability and characterization of hot-melt extruded poly(ethylene oxide) films. J Pharm Sci, 2005. 94(10): p. 2232-45.
Raymond, E.G., et al., Acceptability of five nonoxynol-9 spermicides. Contraception, 2005. 71(6): p. 438-42.
Repka, M.A. and J.W. McGinity, Bioadhesive properties of hydroxypropylcellulose topical films produced by hot-melt extrusion. J Control Release, 2001. 70(3): p. 341-51.
Repka, M.A. and J.W. McGinity, Influence of vitamin E TPGS on the properties of hydrophilic films produced by hot-melt extrusion. International journal of pharmaceutics, 2000. 202(1): p. 63-70.
Repka, M.A., et al., Characterization of cellulosic hot-melt extruded films containing lidocaine. Eur J Pharm Biopharm, 2005. 59(1): p. 189-96.
Repka, M.A., et al., Influence of plasticizers and drugs on the physical-mechanical properties of hydroxypropylcellulose films prepared by hot melt extrusion. Drug development and industrial pharmacy, 1999. 25(5): p. 625-633.
Repka, M.A., et al., Pharmaceutical applications of hot-melt extrusion: Part II. Drug Dev Ind Pharm, 2007. 33(10): p. 1043-57.
Repka, M.A., S. Prodduturi, and S.P. Stodghill, Production and characterization of hot-melt extruded films containing clotrimazole. Drug Dev Ind Pharm, 2003. 29(7): p. 757-65.
Rohan, L.C. and A.B. Sassi, Vaginal drug delivery systems for HIV prevention. AAPS J, 2009. 11(1): p. 78-87.
Romano, J., et al. Sustained delivery of the microbicide dapivirine using intra-vaginal rings: An Independent clinical assessments of drug delivery and safety in women. in 14th Conference on Retroviruses and Opportunistic Infections. 2007. Poster #1000.
Romano, J., et al., Microbicide delivery: formulation technologies and strategies. Curr Opin HIV AIDS, 2008. 3(5): p. 558-66.
Romano, J., et al., Safety and availability of dapivirine (TMC120) delivered from an intravaginal ring. AIDS research and human retroviruses, 2009. 25(5): p. 483-488.
Royce, R.A., et al., Sexual transmission of HIV. N Engl J Med, 1997. 336(15): p. 1072-8.
Sassi, A., et al., Formulation development of retrocyclin 1 analog RC-101 as an anti-HIV vaginal microbicide product. Antimicrobial agents and chemotherapy, 2011. 55(5): p. 2282-2289.
Schmidt, P.C. and F. Niemann, The MiniWiD-coater. III. Effect of application temperature on the dissolution profile of sustained-release theophylline pellets coated with Eudragit RS 30 D. Drug development and industrial pharmacy, 1993. 19(13): p. 1603-1612.
Shah, K.R., S.A. Chaudhary, and T.A. Mehta, Polyox (polyethylene oxide) multifunctional polymer in novel drug delivery system. IJPSDR, 2014. 6: p. 9.
Srikrishna, S. and L. Cardozo, The vagina as a route for drug delivery: a review. Int Urogynecol J, 2013. 24(4): p. 537-43.
Sudeendra, B.R., et al., Development and characterization of bioadhesive vaginal films of clotrimazole for vaginal candidiasis. Acta Pharm Sci, 2010. 52: p. 417-26.
Taha, T.E., et al., Bacterial vaginosis and disturbances of vaginal flora: association with increased acquisition of HIV. AIDS, 1998. 12(13): p. 1699-706.

(56) References Cited

OTHER PUBLICATIONS

Thurman, A.R., M.R. Clark, and G.F. Doncel, Multipurpose prevention technologies: biomedical tools to prevent HIV-1, HSV-2, and unintended pregnancies. Infect Dis Obstet Gynecol, 2011. 2011: p. 1-10.

Van der Straten, A., et al., Women's experiences with oral and vaginal pre-exposure prophylaxis: the VOICE-C qualitative study in Johannesburg, South Africa. PLoS One, 2014. 9(2): p. e89118.

Van Gaal, E.V.B., et al., Flow cytometry for rapid size determination and sorting of nucleic acid containing nanoparticles in biological fluids. Journal of Controlled Release, 2010. 141(3): p. 328-338.

Vermani, K. and S. Garg, The scope and potential of vaginal drug delivery. Pharm Sci Technolo Today, 2000. 3(10): p. 359-364.

Vervaet, Chris, Lieven Baert, and Jean Paul Remon. Extrusion-spheronisation a literature review. International journal of pharmaceutics 116.2(1995): 131-146.

Vynckier, A.K., et al., Hot-melt co-extrusion: requirements, challenges and opportunities for pharmaceutical applications. Journal of Pharmacy and Pharmacology, 2014. 66(2): p. 167-179.

Walker, P.R., et al., Epidemiology: Sexual transmission of HIV in Africa. Nature, 2003. 422(6933): p. 679.

Woolfson, A.D., R.K. Malcolm, and R. Gallagher, Drug delivery by the intravaginal route. Critical Reviews™ in Therapeutic Drug Carrier Systems, 2000. 17(5), 505-555.

Young, C.R., J.J. Koleng, and J.W. McGinity, Production of spherical pellets by a hot-melt extrusion and spheronization process. International journal of pharmaceutics, 2002. 242(1): p. 87-92.

International Search Report and Written Opinion dated Oct. 25, 2018, from International Application No. PCT/US2018/040012, 13 pages.

* cited by examiner

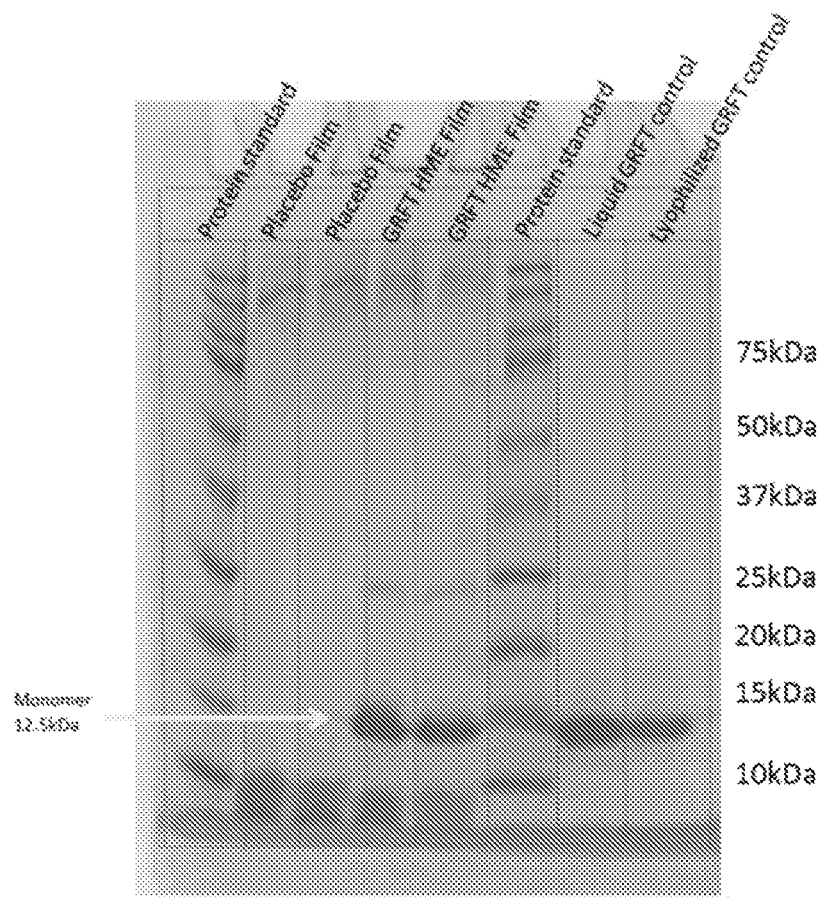
FIG. 4
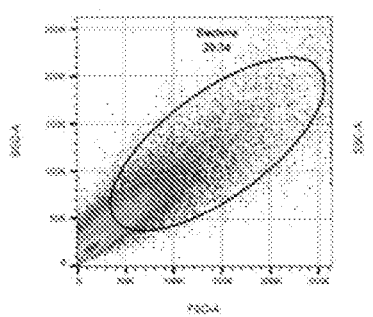 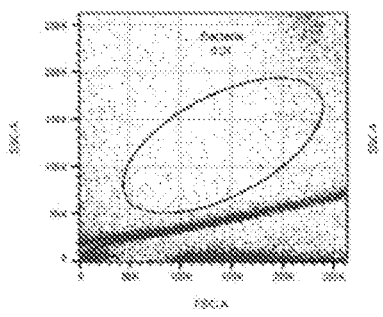 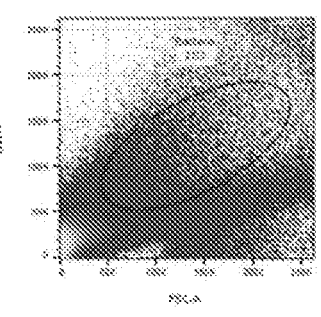
FIG. 5A        FIG. 5B        FIG. 5C

HOT MELT EXTRUSION FOR PHARMACEUTICAL VAGINAL FILM PRODUCTS

ACKNOWLEDGEMENT OF GOVERNMENT SUPPORT

This invention was made with government support under Grant No. AI082639 awarded by the National Institutes of Health. The government has certain rights in the invention.

BACKGROUND

Vaginal drug delivery is an important route for local and systemic drug administration. There are several advantages of the vaginal route for delivery of pharmacologically active agents such as its large surface area and the rich blood supply of the vaginal mucosa (Ndesendo, V. M., et al., *A review of current intravaginal drug delivery approaches employed for the prophylaxis of HIV/AIDS and prevention of sexually transmitted infections*. AAPS Pharm. Sci. Tech., 2008, 9(2):505-201). Topical dosage administration by this route is noninvasive and can avoid first pass metabolism as well as side effects that are caused by systematic exposure (Id.; Ferguson, L. M. and L. C. Rohan, *The importance of the vaginal delivery route for antiretrovirals in HIV prevention*. Ther Deliv, 2011, 2(12):1535-50). Many agents have been administered vaginally, such as antivirals, labor inducing agents, contraceptives, and hormone replacement therapy (Id.; Vermani, K. and S. Garg, *The scope and potential of vaginal drug delivery*. Pharm. Sci. Tech. Today, 2000, 3(10):359-364). Additionally, local targeted vaginal products have been developed including antimicrobials, antifungals, antiprotozoals, and spermicidal agents. Several dosage forms that are commonly used for the delivery of these compounds via the vaginal route include creams, gels, inserts, foams, ointments, douches, vaginal ring, and vaginal films (Woolfson, A. D., et al., *Drug delivery by the intravaginal route*. Crit. Rev. Therapeutic Drug Carrier Systems, 2000, 17(5); Hussain, A. and F. Ahsan, *The vagina as a route for systemic drug delivery*. J. Control Release, 2005, 103(2):301-13; Vermani, K. and S. Garg, *The scope and potential of vaginal drug delivery*. Pharm. Sci. Tech. Today, 2000, 3(10):359-364).

Some of these dosage forms are associated with leakage, messiness, and low residence time of the active pharmaceutical ingredient due to the turn-over of the vaginal epithelium (Rohan, L. C. and A. B. Sassi, *Vaginal drug delivery systems for HIV prevention*. AAPS J., 2009, 11(1):78-87). Major challenges for formulation require maintaining crucial criteria for successful vaginal delivery of the dosage form including interaction of the product with the vaginal content, product dispersion throughout the vagina, release profile of the active agent, and effect on the targets (Machado, R. M., et al., *Vaginal Films for Drug Delivery*. J. Pharm. Sci., 2013, 102(7):2069-2081).

Vaginal films are a desirable strategy for administration of drugs and other agents by this route. Polymeric thin films offer a delivery system, which is thin, soft, and flexible. The films are a self-administered product; they are safe for the vaginal environment and can deliver an adequate amount of active agents. Currently marketed vaginal films are rectangular or square shaped, with a homogenous and soft surface. Many advantages of the vaginal film make it an acceptable dosage form among women, as was reported in several studies (Nel, A. M., et al., *Acceptability of vaginal film, soft-gel capsule, and tablet as potential microbicide delivery methods among African women*. J. Womens Health (Larchmt), 2011, 20(8):1207-14; Elias, C. and C. Coggins, *Acceptability research on female-controlled barrier methods to prevent heterosexual transmission of HIV: Where have we been? Where are we going?* J. Womens Health Gend. Based Med., 2001, 10(2):163-73; Raymond, E. G., et al., *Acceptability of five nonoxynol-9 spermicides*. Contraception, 2005, 71(6):438-42). Advantages of films include their discreet nature, minimal product leakage during use, no requirement for an applicator, low product volume with minimal impact on the innate protective factors in the vagina, potential for both rapid or controlled drug release, and minimal packaging, all which make it a very desirable dosage form (Machado, R. M., et al., *Vaginal Films for Drug Delivery*. J. Pharm. Sci., 2013, 102(7):2069-2081). Furthermore, vaginal films allow accurate dose administration and can be used to stabilize drugs susceptible to degradation in other dosage forms (Rohan, L. C., et al., *Vaginal drug delivery systems for HIV prevention*. AAPS J., 2009, 11(1): 78-87 29; Romano, J., et al., *Microbicide delivery: formulation technologies and strategies*. Curr. Opin. HIV AIDS, 2008, 3(5):558-66; Nel, A. M., et al., *Acceptability of vaginal film, soft-gel capsule, and tablet as potential microbicide delivery methods among African women*. J. Womens Health (Larchmt), 2011, 20(8):1207-14; Elias, C. and C. Coggins, *Acceptability research on female-controlled barrier methods to prevent heterosexual transmission of HIV: Where have we been? Where are we going?* J. Womens Health Gend. Based Med., 2001, 10(2):163-73).

Vaginal films have been investigated in recent years for contraceptive, microbicidal, antifungal, and antimicrobial applications (Garg, S., et al., *Development and characterization of bioadhesive vaginal films of sodium polystyrene sulfonate (PSS), a novel contraceptive antimicrobial agent*. Pharm. Res., 2005, 22(4):584-95; Mishra, R., et al., *Formulation, development and characterization of mucoadhesive film for treatment of vaginal candidiasis*. Int. J. Pharm. Investig, 2016, 6(1):47-55). Such films are manufactured using solvent casting techniques, which involves the use of aqueous or organic solvent (Aitken-Nichol, C., F. Zhang, and J. W. McGinity, *Hot melt extrusion of acrylic films*. Pharm. Res., 1996, 13(5):804-808). For film production, the solvent casting technique faces several problems, as reported by Guitierrez-Rocca et al. (Gutierrez-Rocca, J. C. and J. W. Mcginity, *Influence of aging on the physical-mechanical properties of acrylic resin films cast from aqueous dispersions and organic solutions*. Drug Dev. Indus. Pharm., 1993, 19(3):315-332). Acrylic films manufactured by solvent casting for stability evaluation, had increased tensile strength and decreased elongation and elasticity over time. In addition, it was reported that the level and type of plasticizer, curing time, and temperature have a significant effect on the dissolution rate of drug from solvent casted films (Schmidt, P. C. and F. Niemann, *The MiniWiD-coater. III. Effect of application temperature on the dissolution profile of sustained-release theophylline pellets coated with Eudragit RS 30 D*. Drug Dev. Indus. Pharm., 1993, 19(13): 1603-1612). What are thus needed are new methods of preparing vaginal films, as well as new vaginal film compositions. The methods, compositions, and devices disclosed herein address these and other needs.

SUMMARY

In accordance with the purposes of the disclosed compositions and methods, as embodied and broadly described herein, the disclosed subject matter relates to compositions and methods of making and using the compositions. More specifically, according to the aspects illustrated herein, disclosed are methods of preparing a vaginal drug delivery film, comprising extruding a composition comprising one or more active pharmaceutical ingredients and one or more polymer carriers at an elevated temperature through a die to thereby provide the film. Vaginal drug delivery films prepared by hot melt extrusion are also disclosed, as are methods of using the films to treat various conditions.

Additional advantages of the disclosed compositions and methods will be set forth in part in the description which follows, and in part will be obvious from the description. The advantages of the disclosed compositions will be realized and attained by means of the elements and combinations particularly pointed out in the appended claims. It is to be understood that both the foregoing general description and the following detailed description are exemplary and explanatory only and are not restrictive of the disclosed compositions, as claimed.

BRIEF DESCRIPTION OF THE FIGURES

The accompanying figures, which are incorporated in and constitute a part of this specification, illustrate several aspects of the disclosure, and together with the description, serve to explain the principles of the disclosure.

FIG. 4 shows a SDS-PAGE gel for molecular mass comparisons of GRFT. Lanes (from left) 1 and 6 contain the protein molecular weight markers. Lanes 2 and 3 contain placebo HME film. Lanes 4 and 5 contain GRFT HME film. Lane 7 contains GRFT drug substance. Lane 8 contains lyophilized GRFT reconstituted in media.

FIGS. 5A-5C depict flow cytometer separation of *L. jensenii* and polymeric film. FIG. 5A is from the bacteria population, FIG. 5B is from a placebo film, and FIG. 5C is from a film containing bacteria at T=45 minutes. The dissolution test was conducted using an LSRII flow cytometer. The peak bacterial release was observed after 30 minutes.

FIG. 6A shows DPV release profile from the single entity film and combination films (single and multi-layer film). FIG. 6B shows the release profile of LNG from the single entity film, and combination film (single and multi-layer film).

DETAILED DESCRIPTION

Figure 1:
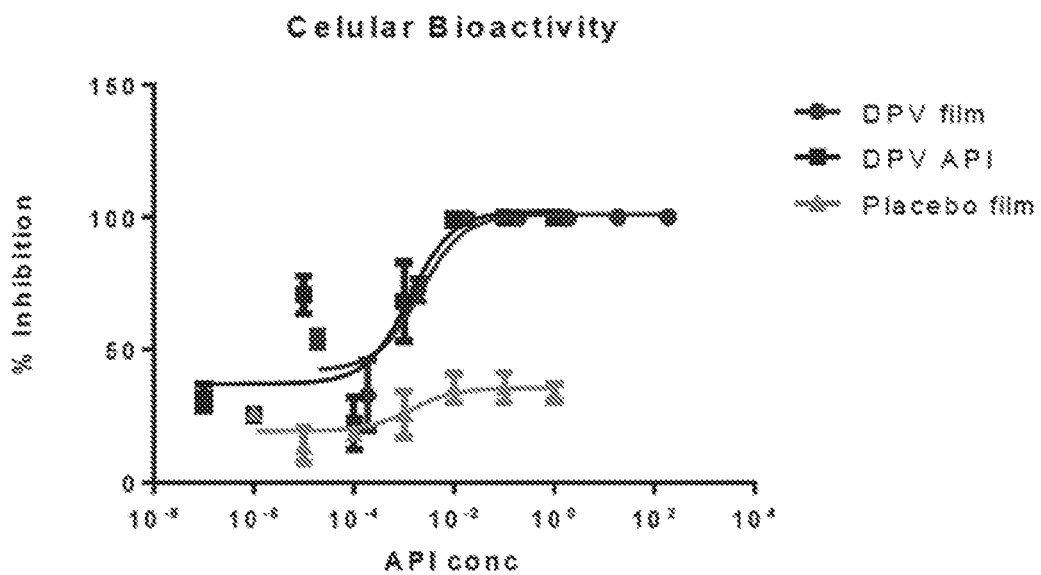
FIG. 1 shows in vitro bioactivity of DPV HME films in TZM-bl cellular assay. DPV HME film, drug substance, and placebo films. DPV HME film maintained similar $IC_{50}$ of 2.0 nM compared to the DPV drug substance. The placebo film demonstrated minimal but quantifiable anti-HIV activity. This is due to the presence of the placebo polymers in the cellular assay.
Figure 2A:
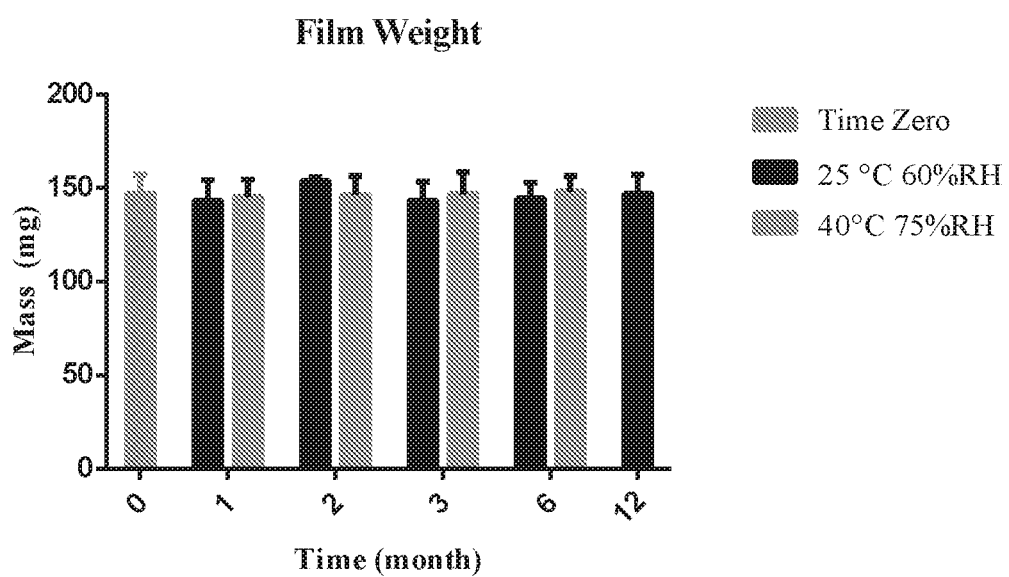
FIGS. 2A-2D show DPV film weight, drug content, puncture strength over the course of a stability study. No changes were observed in the film mass over time determined by measuring film weight or drug content over the testing time. Data presented as mean±SD with a p value <0.05 was considered statistically significant. Drug release profile for the formulation is also shown.
Figure 2B:
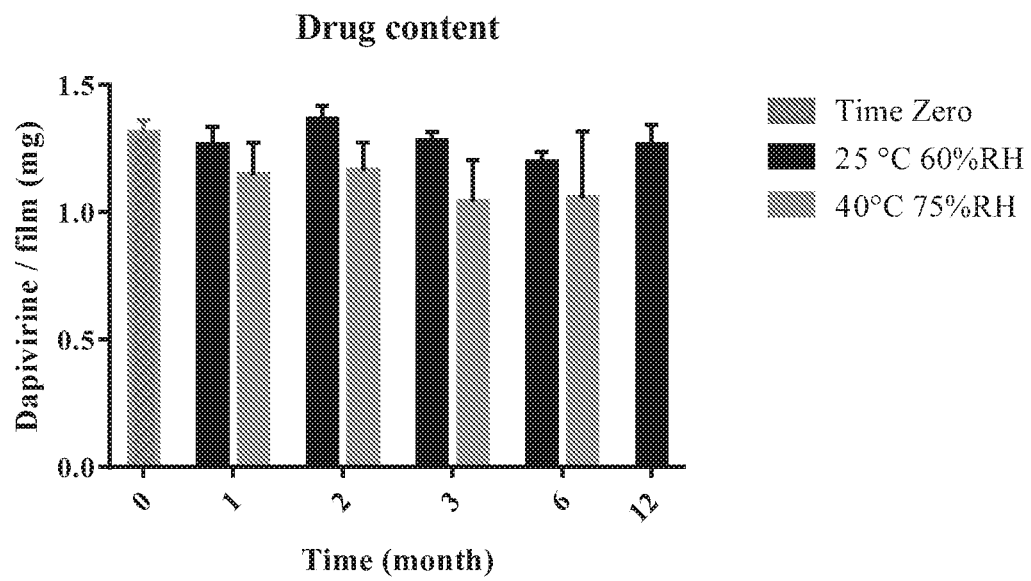
Figure 2C:
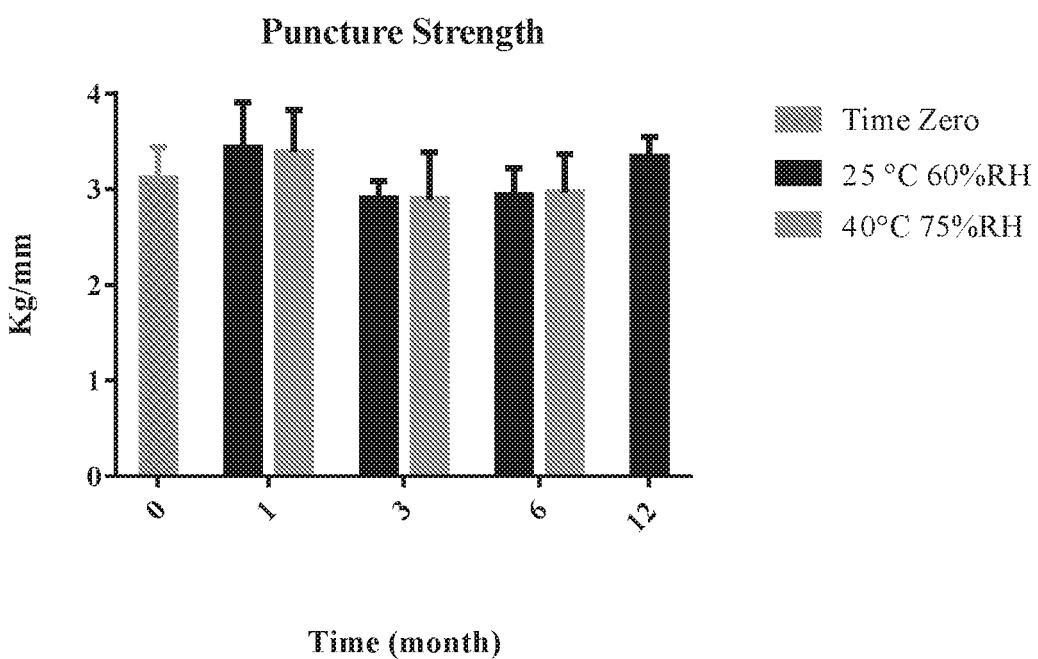
Figure 2D:
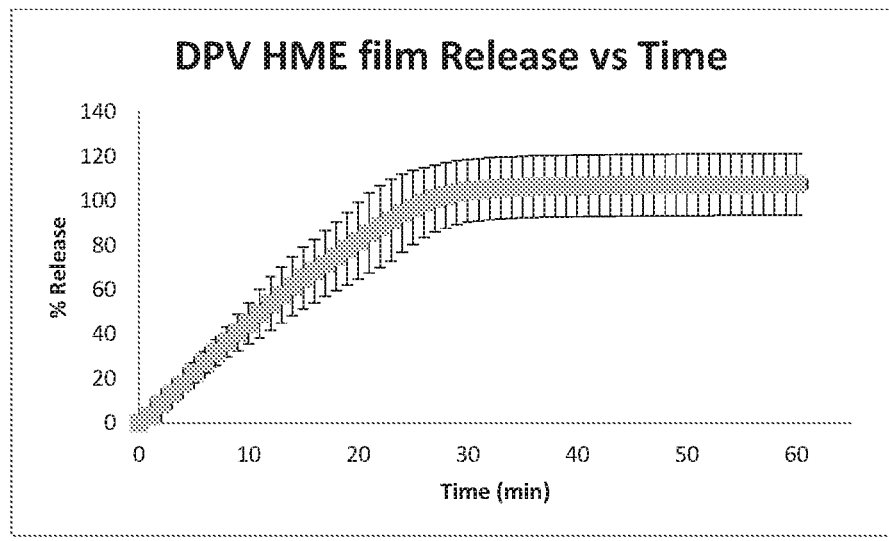

Before the present, methods, compositions and devices are disclosed and described, it is to be understood that the aspects described below are not limited to specific synthetic methods or specific reagents, as such may, of course, vary. It is also to be understood that the terminology used herein is for describing particular aspects only and is not intended to be limiting.

Also, throughout this specification, various publications are referenced. The disclosures of these publications in their entireties are hereby incorporated by reference into this application to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., viral replication, microbial growth, etc.). It is understood that this is typically in relation to some standard or expected value, in other words it is relative, but that it is not always necessary for the standard or relative value to be referred to. For example, "reduces viral replication" means reducing the rate of replication of a virus relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, inhibit, or eliminate a particular characteristic or event (e.g., viral replication, microbial growth, etc.). The term "control" is used synonymously with the term "treat."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

HME

Disclosed herein are vaginal films comprising one or more active pharmaceutical ingredients, e.g., antivirals, antimicrobials, contraceptives, spermicides, and/or microorganisms, peptides, proteins, saccharides, oligonucleotides, etc. in a carrier polymer. Optional ingredients can also be included. The disclosed vaginal films are prepared by hot melt extrusion (HME). HME provides a way to manufacture single or multilayer vaginal films for multiple therapeutic applications. Because HME is widely used in other industries, the disclosed HME methods can be used for local manufacturing in countries with limited resources, thereby decreasing the need for the importation or exportation of highly efficient pharmaceutical products. Also, HME film development requires less time than solvent cast film development since neither the active pharmaceutical ingredient nor the other excipients require solubilization to be formulated into the film dosage form. Low solvent use in the HME production eliminates the drying time required in the solvent cast production. This allows for a smaller manufacturing footprint, and faster film production as well. In addition, casted films often contain residual solvent that can lead to issues with compendial compliance.

The application of HME to the field of vaginal pharmaceutics is beneficial not only through the conservation of resources, but also through the ease of manufacturing scalability. Transition from small bench scale manufacturing to large batch manufacturing has proven to be a hurdle in pharmaceutical development and manufacturing, especially in solvent cast film manufacture. The HME scale-up is simple compared to the solvent cast as it is a dry process where no (or little) fluid dynamic is involved. There are minimal differences between most HMEs regardless of their use for small- or large-scale manufacturing, which aids transitions during scale-up.

During HME, the active pharmaceutical ingredients are melted, mixed, and dispersed into various polymer matrices with or without other ingredients. The extrusion process uses high temperature, pressure, shear, and physical mixing of solids as opposed to other methods that rely on solubilization, dispersion, and other physiochemical properties to create uniform mixtures (Breitenbach, J., *Melt extrusion: from process to drug delivery technology*. Eur. J. Pharm. Biopharm., 2002, 54(2):107-17; Crowley, M. M., et al., *Pharmaceutical applications of hot-melt extrusion: part I*. Drug Dev Ind. Pharm., 2007, 33(9):909-26). HME has been found to be an extremely useful technology in the pharmaceutical industry because of its robust production, reproducibility, product uniformity, and ability to accommodate a wide range of active pharmaceutical ingredients regardless of Biopharmaceutics Classification System (BCS) class (Srikrishna, S. and L. Cardozo, *The vagina as a route for drug delivery: a review*. Intr. Urogynecol J., 2013, 24(4): 537-43).

Extruders that are suitable for use herein comprise various parts: 1) the feed hopper (used to feed the raw material to the extruder barrel under controlled speed), 2) the conveying and mixing system (screws, temperature control barrel), 3) the die system for forming the shape of the dosage form, and 4) the downstream auxiliary equipment for cooling, collecting, and cutting the extrudate (Breitenbach, J., *Melt extrusion: from process to drug delivery technology*. Eur. J. Pharm. Biopharm., 2002, 54(2):107-17).

There are two general types of conveying and mixing systems: single screw and twin screw. With single screw extrusion one screw rotates inside an extruder barrel and is utilized for feeding, melting, and mixing. Twin-screw extrusion uses two screws rotating inside the extruder barrel. The twin screws can be co-rotating (rotating in the same direction) or counter rotating (opposite direction) (Jani, R. and D. Patel, *Hot melt extrusion: An industrially feasible approach for casting orodispersible film*. Asian J. Pharm. Sci., 2015, 10(4):292-305). The co-rotating screws can work at elevated speed allowing high output necessary for sufficient mixing. The counter rotating screws are used to generate high shear. Due to the nature of mixing using counter rotating screws air entrapment and high pressure may occur. Twin screw extruders have several advantages over the single screw extruders, such as easier feeding of material, better kneading and dispersing capacities, less tendency to overheat, and shorter transit times. Either single- or twin-screw extruders can be used in the disclosed methods.

The barrel collects the materials from the feed hopper and is responsible for temperature maintenance and mixing. Mixing is carried out by the screw(s), which are housed within the barrel. These screws, typically made of stainless steel, continuously turn within the barrel, allowing for mixing of the raw material. The screws can be designed with multiple different elements that allow for different functions. Three common screw elements are the mixing element, the compressing element, and the metering element. These elements are selected based on the desired final product. As the raw material passes through the barrel and encounters the designed screw elements, it is melted, mixed, and pushed through the die.

The die system is attached to the end of the barrel and its shape designed to the desired shape of each dosage form. The die is generally made of stainless steel, to minimize reactivity to the material and to allow sufficient cleaning. The die controls the shape of the dosage form, for example, a film die (also known as flat die) is used for film manufacturing, which allows for the extrusion of the film sheet at the desired thickness. For downstream processing, a variety of cooling equipment can be used to collect the extruded product, depending on the dosage form. For example, chilled rolls are used to rapidly cool down and collect an extruded film sheet. Once cooled, the film sheet is collected and cut and packed into the desired film shape and unit dose.

The extrusion can be conducted at an elevated temperature, e.g., from 40° C. to 250° C., from 45° C. to 225° C., from 50° C. to 200° C., from 55° C. to 175° C., from 60° C. to 150° C., from 65° C. to 145° C., from 70° C. to 140° C., from 75° C. to 135° C., from 80° C. to 130° C., from 85° C. to 125° C., from 90° C. to 120° C., from 95° C. to 115° C., from 100° C. to 150° C., from 100° C. to 250° C., from 125° C. to 225° C., from 150° C. to 200° C., from 175° C. to 250° C., or from 110° C. to 140° C.

HME offers several manufacturing advantages over the solvent casting technique. HME can provide a solvent-free process that is suitable for moisture-sensitive drugs and hydrophobic active pharmaceutical ingredients as it can enhance solubility and bioavailability of water insoluble active agents. Additionally, the lack of need for volatile solvents makes it easier and safer for the scientists to handle. This process is more economically beneficial than solvent cast due to its reduced production time, fewer processing steps, and continuous operation. It may be applied to sustained, modified, and targeted release drug delivery systems. Moreover, HME allows for more specific mixing than solvent cast. While solvent cast requires all components to be mixed in solvent prior to casting, HME can utilize a wide range of screw elements that can be designed to achieve specific mixing conditions for process optimization. These screws are also self-wiping, which makes cleaning and cleaning validation easier. Likewise, the lack of fluid dynamics involved in the process can make scale-up less challenging than solvent based manufacturing methods. Finally, because in the HME process the active pharmaceutical ingredient has a short residence time in the mixing chamber (barrel), its exposed to these potentially harmful processes is limited. This can increase stability and reduce degradation in the final product.

Carriers

Film forming polymers are used as the carriers in the disclosed methods. Selection of a polymer for the extrusion process should consider polymer stability, drug-polymer miscibility, and the end function of the dosage form, which must meet the goal of the target product profile. For example, to create quick dissolving films, a polymer that can disintegrate and release the active pharmaceutical ingredient quickly can be selected. Additionally, the polymer's melting point and glass transition state ($T_g$) should suit the process parameters of the selected product. The selected polymers should be non-toxic, non-irritating, and follow Generally Recognized as Safe (GRAS) guidelines. The selected polymer should also be stable under elevated temperature and pressures, possess thermoplastic behavior, and maintain a low toxicity profile.

Several polymers with film forming properties have been determined to be well suited for the disclosed HME processes. In specific examples disclosed herein, high molecular weight polyethylene oxide (PEO), a crystalline polymer that is available in a range of from 100,000 to 7,000,000 Da molecular weight, is suitable for the extrusion process of film due to its large processing window (Shah, K. R., S. A. Chaudhary, and T. A. Mehta, *Polyox (polyethylene oxide) multifunctional polymer in novel drug delivery system.* IJPSDR, 2014, 6:9; Dhawan, S., et al., *Application of poly (ethylene oxide) in drug delivery systems.* Pharm. Tech., 2005, 29:82-96). Specific examples of suitable high molecular weight polyethylene oxide that can be used is termed PolyOx, e.g., POLYOX™N80, which has a MW of about 200,000 Da, or POLYOX™N-10, which has a molecular weight of about 100,000 Da. Also, PEO was reported by Bruce et al. to possess a low processing temperature, which can be beneficial for heat sensitive active pharmaceutical ingredients.

Further, the disclosed high molecular weight PEO can be combined with a medium molecular weight PEO that is available in a range of from 2000 to 8000 Da. Specific examples of suitable medium molecular weight PEO that can be used are PEG (polyethylene glycol) 2000, PEG4000, PEG6000, and PEG8000, which have molecular weights of about 2000, 4000, 6000, and 8000 Da, respectively.

Another example of a suitable film forming polymer is hydroxypropylcellulose (HPC), which is a semicrystalline non-ionic water soluble cellulose base polymer. It has dual solubility in aqueous solutions and polar organic solvents. KLUCEL™ HPC EF and KLUCEL™ HPC LF are the most widely applied polymers for film since they can be processed at temperatures as low as 100° C.

Polyethylene oxide (PEO) and hydroxypropyl cellulose (HPC) are film forming polymers that are desirable for HME film manufacturing since they are both approved for pharmaceutical and food use and have a low softening temperature. The HME manufacture should take place when the polymer is in the molten state. This would imply when the process temperature is maintained above the glass temperature and sometimes above the melting temperature of the polymer. Both polymers have low $T_g$ (i.e., PEO $T_g$=−30° C. and HPC $T_g$=0° C.) and low $T_m$ (i.e., PEO $T_m$=65° C., HPC $T_m$=135-140° C.), which allows for the HME manufacture at relative low process temperatures, while maintaining the final soft extrudate.

Additional polymers can be included with the combined high and medium molecular weight PEO and optionally HPC disclosed herein to adjust the melt, mechanical, and biological properties. For example, polyvinyl pyrrolidone (PVP), hydroxyethyl cellulose (HEC), hydroxypropylmethyl cellulose (HPMC), and any combination thereof can be added. In still further examples, suitable additional polymers for use herein include cellulose polymers such as copolymers of vinyl pyrrolidone and vinyl acetate, poly(hydroxyalkyl methacrylate), poly (vinyl alcohol), polyacrylamides, polyacrylic acid, agar, alginates, casein, carrageenan, gelatin, gellan gum, guar gum, gum acacia, microbial polysaccharides, such as dextran, xanthan gum, pullulan, and the like, and any combination thereof.

Often, a mixture of different types of polymer, resulting in a controlled swelling, is desirable. Particularly preferred are mixtures of high and medium molecular weight polyethylene oxide (PEO) and optionally hydroxypropyl cellulose (HPC). In more specific examples, mixtures of high molecular weight PEO and one or more medium molecular weight PEO can be used. In such examples, the high molecular weight PEO can be POLYOX™ and have a molecular weight of from 100,000 to 700,000 Da, e.g., POLYOX™ N-80 (polyethylene oxide with a molecular weight of about 200,000 Da) or POLYOX™ N-10 (polyethylene oxide with a molecular weight of about 100,000 Da), including combinations thereof. The medium molecular weight PEO can have a molecular weight of from 2000 to 8000 Da, e.g., PEG2000, PEG4000, PEG6000, or PEG8000, including combinations thereof.

Still further, the following additional ingredients can be mixed with the carriers: lecithin, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxypropylmethycellulose phthalate, noncrystalline cellulose, magnesium aluminum silicate, triethanolamine, sugars and starches polydimethyl siloxanes, modified polydimethyl siloxanes, ethylene/vinyl acetate copolymers (EVA), polyethylene, polypropylene, acrylic acid polymers, polytetrafluoroethylene (PTFE), polyurethanes, poly(methacrylate), polymethyl methacrylate, poly(hydroxyethylmethacrylate) (pHEMA), polyhydroxy alkanoates, poly(lactic acid), poly(glycolic acid), hydrophilic polymers such as the hydrophilic hydrogels, cross-linked polyvinyl alcohol and combinations thereof.

In specific examples, the total amount of carrier polymers in the film can be from 50% to 99%, e.g., from 50% to 95%, from 50% to 90%, from 50% to 85%, from 50% to 80%, from 50% to 75%, from 50% to 70%, from 50% to 65%, from 65% to 99%, from 65% to 95%, from 65% to 90%, from 65% to 85%, from 65% to 80%, from 65% to 75%, from 65% to 70%, from 70% to 99%, from 70% to 95%, from 70% to 90%, from 70% to 85%, from 70% to 80%, from 80% to 99%, from 80% to 95%, from 80% to 90%, from 90% to 99%, from 90% to 95%, or from 95% to 99% (w/w).

In specific examples, the high molecular weight polyethylene oxide with a molecular weight range of 100,000 to 7,000,000 Da ("POLYOX™") can be present in the film in an amount of from 30% to 60%, e.g., from 30% to 55%, from 30% to 50%, from 30% to 45%, from 30% to 40%, from 30% to 35%, from 35% to 60%, from 35% to 55%, from 35% to 50%, from 35% to 45%, from 35% to 40%, from 40% to 60%, from 40% to 55%, from 40% to 50%, from 40% to 45%, from 45% to 60%, from 45% to 55%, from 45% to 50%, from 50% to 60%, from 50% to 55%, or from 55% to 60% by weight.

In specific examples, the medium molecular weight polyethylene oxide having a molecular weight of from 2000 to 8000 Da can be present in an amount of from 15% to 30%, e.g., from 15% to 25%, from 15% to 20%, from 20% to 30%, from 20% to 25%, or from 25% to 30% by weight.

In some examples, there is no HPC present in the film. In other examples, HPC can be present in an amount of from 30% to 60%, e.g., from 30% to 55%, from 30% to 50%, from 30% to 45%, from 30% to 40%, from 30% to 35%, from 35% to 60%, from 35% to 55%, from 35% to 50%, from 35% to 45%, from 35% to 40%, from 40% to 60%, from 40% to 55%, from 40% to 50%, from 40% to 45%, from 45% to 60%, from 45% to 55%, from 45% to 50%, from 50% to 60%, from 50% to 55%, or from 55% to 60% by weight.

In still further examples, the carrier can comprise a low molecular weight polyethylene oxide having a molecular weight from 200 to 600 Da. In specific examples, the low molecular weight PEO has a molecular weight of about 400 Da. The low molecular weight PEO can be present in the film in an amount of from 1% to 4%, e.g., from 1% to 3%, from 1% to 2%, from 2% to 4%, from 2% to 3%, or from 3% to 4% by weight.

Disintegrants

In addition, disintegration agents (e.g., medium MW Polyethylene glycols) can be used to enhance the speed of the disintegration and the drug release, as required for the dosage form (Garg, S., et al., *Advances in development, scale-up and manufacturing of microbicide gels, films, and tablets*. Antiviral Res., 2010, 88 Suppl 1:S19-29).

Additional examples of disintegration agents that can be used are sodium starch glycolate (EXPLOTAB™, PRIMOJEL™) and croscarmellose sodium (AC-DI-SOL™) which we have discovered effectively enhance the moisture absorbing capacity of the film, a property which is particularly desirable for wound care applications. Other suitable absorbents include cross-linked PVP (POLYPLASDONE™ XL 10), veegum, clays, alginates, PVP, alginic acid, carboxymethylcellulose calcium, microcrystalline cellulose (e.g., AVICEL™), polacrillin potassiium (e.g., AMBERLITE™), sodium alginate, corn starch, potato starch, pregelatinized starch, modified starch, cellulosic agents, montmorrilonite clays (e.g., bentonite), gums, agar, locust bean gum, gum karaya, pecitin, tragacanth, and other disintegrants known in to those of ordinary skill in the art. When present, the super-disintegrant (or absorbents) will be present in the range of about 0.1-20% wt. based upon the weight of the film.

Plasticizers

Since polymers with high molecular weight can have high melt viscosity and $T_g$, and thus become difficult to extrude, plasticizers can be used as part of the film formulation. Plasticizers are low molecular weight compounds that can be added to the formulation to increase the plasticity, soften the polymer carrier, and enhance the flexibility of the final product. The addition of plasticizers to the formulation can improve the manufacturing conditions or the physiochemical properties of the film. The addition of a plasticizer can lower the $T_g$ of the carrier polymer by increasing the free volume between polymer chains and, in turn, lowering the process manufacturing temperature (Aharoni, S. M., *Increased glass transition temperature in motionally constrained semicrystalline polymers*. Polymers for Advanced Technologies, 1998, 9(3):169-201). A lower processing temperature can enhance the stability profile of the polymer carrier and active pharmaceutical ingredient. Some suitable plasticizers that can be used for the disclosed HME processes are triacetin, low molecular weight polyethylene glycols, and citrate. Additional examples of plasticizers are glycerin and propylene glycol. It should also be noted that some active pharmaceutical ingredients can have intrinsic plasticizer functionality in the HME process (Repka, M. A., et al., *Influence of plasticizers and drugs on the physical-mechanical properties of hydroxypropylcellulose films prepared by hot melt extrusion*. Drug Dev. Indus. Pharm., 1999, 25(5):625-633). Plasticizers can affect the drug release rate of extruded dosage forms and long-term stability of the final product. Although the elevated process temperature in HME can be reduced by the addition of plasticizer, polymer and active pharmaceutical ingredient stability may still be affected.

In specific examples, the plasticizers can be present in the film in an amount of from 0% to 5%, e.g., from 0.1% to 4%, from 0.1% to 3%, from 0.1% to 2%, from 0.1% to 1%, from 0.1% to 1%, from 1% to 5%, from 1% to 4%, from 1% to 3%, from 1% to 2%, from 2% to 5%, from 2% to 4%, from 2% to 3%, from 3% to 5%, from 3% to 4%, from 4% to 5% (w/w). In certain examples, there are no plasticizers (0%) in the film.

Antioxidants

Antioxidants are molecules that can inhibit oxidation. They can be added to the disclosed formulations to enhance stability under high heat and shear produced by the HME process. Antioxidants can be divided into two main categories based on their mechanism of action: (1) preventative antioxidants and (2) chain-breaking antioxidants. Preventative antioxidants prevent the initiation of a free radical chain reaction. Ascorbic acid is an example of a preventative antioxidant. This is a vitamin that can undergo oxidation and react with free radicals. The free radical can impact drug degradation. The self-reduction properties of preventative antioxidants can interfere with autoxidation and protect the drug and the formulation from oxygen molecules. Common chain-breaking antioxidants are hindered phenols and aromatic amines. When a free radical is present a second radical is formed. Then chain-breaking antioxidants cause a third molecule to generate a free radical. The free radical process continues that way until the process terminates and the radical is stabilized by a chain breaking antioxidant or the product decays into stable state. Vitamin E is a common hindered phenol that can be used in the disclosed HME formulations. Additional examples of antioxidants that can be used include ascorbic acid, ascorbyl palmitate, butylated hydroxyanisole, butylated hydroxytoluene, hypophophorous acid, monothioglycerol, sodium ascorbate, sodium formaldehyde sulfoxylate, sodium metabisulfite, vitamin C, sodium bisulfite, and propyl gallate.

In specific examples, the antioxidants can be present in the film in an amount of from 0% to 5%, e.g., from 0.1% to 4%, from 0.1% to 3%, from 0.1% to 2%, from 0.1% to 1%, from 0.1% to 1%, from 1% to 5%, from 1% to 4%, from 1% to 3%, from 1% to 2%, from 2% to 5%, from 2% to 4%, from 2% to 3%, from 3% to 5%, from 3% to 4%, from 4% to 5% (w/w). In certain examples, there are no antioxidants (0%) in the film.

Active Pharmaceutical Ingredients

The disclosed vaginal films can be used to deliver any number of active pharmaceutical ingredients including small molecules, biomolecules, and bacteria. The specific type of active pharmaceutical ingredient depends on the desired end product and use, and whether the active pharmaceutical ingredient can withstand the HME process conditions. Active pharmaceutical ingredients can be synthetic or natural organic compounds, hydrophobic actives, hydrophilic actives, proteins or peptides, oligonucleotides or nucleotides, bacteria, or polysaccharides or sugars. Active pharmaceutical ingredients can have any of a variety of activities, which may be inhibitory or stimulatory, such as antibiotic activity, antiviral activity, antifungal activity, steroidal activity, cytotoxic or anti-proliferative activity, anti-inflammatory activity, analgesic or anesthetic activity, or be useful as contrast or other diagnostic agents. A description of classes of drugs and species within each class can be found in Martindale, *The Extra Pharmacopoeia*, 31st Ed., The Pharmaceutical Press, London (1996) and Goodman and Gilman, *The Pharmacological Basis of Therapeutics*, (9th Ed., McGraw-Hill Publishing company (1996)).

Examples of suitable active pharmaceutical ingredients include dapivirine, metronidazole, griffithsin, contraceptive steroids (e.g., levonorgestrel), and *Lactobacillus*, and any combination thereof. Further examples of suitable active pharmaceutical ingredients include, tenofovir, clotrimazole, benzalkonium chloride, neomycins, such as neomycin-B-sulfite, polymyxins, such as polymyxin-B-sulfate, econazol, econazolnitrate, miconazole, miconazolnitrate, nonxynol-9, octoxynol-9, chlorhexidine, polystyrene sulfonate, NNRTI pyrimidinedione, IQP-0528, RC-101, progestins, estrogens, antiestrogens, antiprogestins, α-adrenergic agonists, lactic acid, polylactic acid, glycolic acid, polyglycolic acid, carbopol, polycarbophil, ascorbic acid, D-pantothenic acid, folic acid and the reduced forms thereof, especially tetrahydrofolates and metabolites of folic acid, preferably 5-methyl-6(S)-tetrahydrofolic acid and its salts such as earth alkaline salts, especially the calcium salt (Metafolin), fumaric acid, benzoic acid, p-aminobenzoic acid, alginic acid, sorbic acid, tartaric acid, edetic acid and salts of the acids, niacinamide, *Bifidobacterium* strains, and any combination thereof.

The active pharmaceutical ingredients can also be *Lactobacillus* species, for example *Lactobacillus jensenii*, *Lactobacillus iners*, *Lactobacillus reuteri*, *Lactobacillus reuterii* RC-14, *Lactobacillus delbrueckii*, *Lactobacillus gasseri*, *Lactobacillus jensenii*, *Lactobacillus catenaforme*, *Lactobacillus paracasei*, *Lactobacillus paracasei* Lbp PB01, *Lactobacillus casei*, *Lactobacillus acidophilus*, *Lactobacillus acidophilus* Lba EB01, *Lactobacillus acidophilus* Lba EB02, *Lactobacillus crispatus*, *Lactobacillus crispatus* CTV05, *Lactobacillus salivarius*, *Lactobacillus brevis*, *Lactobacillus fermentum*, *Lactobacillus fermentum* RC-14, *Lactobacillus fermentum* B-54, *Lactobacillus plantarum*, *Lactobacillus plantarum* Lbp1 PB02, *Lactobacillus* Lbxx EB03, *Lactobacillus* Lbxx PB03, *Lactobacillus rhamnosus*, *Lactobacillus rhamnosus* GR-1, and other genus or strains of *Lactobacillus*, or any combination thereof.

In specific examples, the disclosed vaginal films comprise an antibiotic and a *Lactobacillus* species (e.g., *L. jensenii* and the metronidazole) or an antiretroviral drug and a contraceptive. In further examples, the disclosed vaginal films comprise two or more anti-HIV agents, anti-herpes agents, and/or anti-hepatitis C agents. These different components can be in the same layer or each can be in a different layer of a multilayer film.

In specific examples, the active pharmaceutical ingredient can be present in the film in an amount of from 0.1% to 50%, e.g., e.g., from 0.1% to 45%, from 0.1% to 40%, from 0.1% to 35%, from 0.1% to 30%, from 0.1% to 25%, from 0.1% to 20%, from 0.1% to 15%, from 0.1% to 10%, from 0.1% to 5%, from 0.1% to 1%, from 1 to 50%, from 1% to 45%, from 1% to 40%, from 1% to 35%, from 1% to 30%, from 1% to 25%, from 1% to 20%, from 1% to 15%, from 1% to 10%, from 1% to 5%, from 5% to 50%, from 5% to 45%, from 5% to 40%, from 5% to 35%, from 5% to 30%, from 5% to 25%, from 5% to 20%, from 5% to 15%, from 5% to 10%, from 10% to 50%, from 10% to 45%, from 10% to 40%, from 10% to 35%, from 10% to 30%, from 10% to 25%, from 10% to 20%, from 10% to 15%, from 15% to 50%, from 15% to 45%, from 15% to 40%, from 15% to 35%, from 15% to 30%, from 15% to 25%, from 15% to 20%, from 20% to 50%, from 20% to 45%, from 20% to 40%, from 20% to 35%, from 20% to 30%, from 20% to 25%, from 25% to 50%, from 25% to 45%, from 25% to 40%, from 25% to 35%, from 25% to 30%, from 30% to 50%, from 30% to 45%, from 30% to 40%, from 30% to 35%, from 35% to 50%, from 35% to 45%, from 35% to 40%, from 40% to 50%, from 40% to 45%, or from 45% to 50%

Vaginal Films

The vaginal film dosage form is a highly applicable and widely versatile delivery platform for a variety of active pharmaceutical agents. In several behavioral studies, the advantages of vaginal films, including its discreet use, minimal product leakage, and ease of use, have been shown to contribute to its desirability by women. To date, the commercially-available pharmaceutical films are manufactured using solvent casting techniques. The films disclosed herein are prepared by hot melt extrusion.

The disclosed vaginal films can be a single layer, comprising one or more of the active pharmaceutical ingredients disclosed herein, or can be multiple layers with each layer comprising a different composition of active pharmaceutical ingredient(s).

Vaginal films are comprised of the active pharmaceutical ingredient, carrier polymers, and optional plasticizers, antioxidants, and disintegrants (see Machado, R. M., et al., *Vaginal Films for Drug Delivery*. J. Pharm. Sci., 2013, 102(7):2069-2081). The disclosed vaginal films can comprise any of the carriers, plasticizers, antioxidants, and other excipients disclosed herein.

Films can be categorized based on dissolution speed: 1) fast dissolving films (can release the active agent quickly), 2) modified release (release the active agent less quickly), and 3) slow-disintegrating muco-adhesive films (slow release or controlled release films) (Gang, S., et al., *Advances in development, scale-up and manufacturing of microbicide gels, films, and tablets*. Antiviral Res., 2010, 88 Suppl 1:S19-29). The disclosed vaginal films prepared by HME can be any one of these types of films.

The thickness of the disclosed films can be from 10 μm to 5 mm, e.g., from 10 μm to 500 μm, from 100 μm to 500 μm, from 300 μm to 500 μm, from 10 μm to 700 μm, from 100 μm to 700 μm, from 300 μm to 700 μm, from 500 μm to 700 μm, from 10 μm to 1 mm, from 100 μm to 1 mm, from 300 μm to 1 mm, from 500 μm to 1 mm, from 700 μm to 1 mm, from 10 μm to 5 mm, from 100 μm to 5 mm, from 300 μm to 5 mm, from 500 μm to 5 mm, from 700 μm to 5 mm, or from 1 mm to 5 mm.

The disclosed films can also have less than 10% water, e.g., less than 9%, less than 8%, less than 7%, less than 6%, less than 5%, less than 4%, less than 3% water, less than 2%, less than 1%, or less than 0.5% water.

Methods of Use

The disclosed vaginal films can be used to administer active pharmaceutical ingredients to a subject by applying the film to the subject's vagina. The vaginal route of administration provides ease of use and non-invasiveness, which can prevent tissue damage and potential infection. Administration does not typically require intervention by medical personnel, which reduces the burden of repeated hospital visits and/or appointments with health-care professionals. Furthermore, the vaginal delivery products are usually discrete, which results in minimal interference with daily life. In addition, drugs that are administered vaginally avoid gastrointestinal (GI) absorption, GI side effects, and hepatic first-pass metabolism (Srikrishna, S. and L. Cardozo, *The vagina as a route for drug delivery: a review*. Intr. Urogynecol. J., 2013, 24(4):537-43). The vagina's enzymatic composition is unique, and therefore, drugs designed to undergo enzymatic metabolism after administration may be applicable to vaginal administration. This drug delivery strategy can allow for lower drug dosing levels to achieve sufficient biological effects, reduced toxicity, and evasion of side effects associated with higher dosing levels.

The vaginal route can be used to deliver drugs both systemically and locally. It is efficient in systemic delivery due to its large surface area and rich blood supply (Ndesendo, V. M., et al.). On the other hand, for vaginally-targeted drugs, direct vaginal application reached higher concentrations in the vaginal tract than those via other systemic route (Karim, S. S. A., et al., *Drug concentrations after topical and oral antiretroviral pre-exposure prophylaxis: implications for HIV prevention in women*. Lancet, 2011, 378(9787):279). This is important since vaginal administration of drugs can result in higher drug concentration at the site of action, leading to higher efficacy and treatment for vaginal associated infection (Hussain, A. and F. Ahsan, *The vagina as a route for systemic drug delivery*. J. Control Release, 2005, 103(2):301-13).

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Dapivirine was provided by International Partnership for Microbicides (IPM). Metronidazole was purchased from Spectrum (Gardena, Calif., US). Recombinant Griffithsin was manufactured by Kentucky Bioprocessing LLC (KBP; Owensboro, Ky.) and provided through the University of Louisville. Levonorgestrel was purchased from CHEMO (Chatam, N.J.). POLYOX™ N10, N80 (Polyethylene oxide, MW, 100,000 and 200,000 Da respectively), and Polyethylene glycol 4000 were purchased from Dow Chemical Company (Midland, Mich., USA). KLUCEL™ EF (HPC MW, 100,000 Da) was purchased from Ashland, Inc (Bridgewater, N.J.). Polyethylene glycol 400 and vitamin E acetate were purchased from Spectrum (Gardena, Calif., US). Ultrapure water was obtained from an in-house MilliQ water purification system. Phosphate buffered saline 10× molecular biology grade was purchased from Mediatech, Inc (Manassa, Va.). Acetonitrile (ACN) and trifluoroacetic acid (TFA) were obtained from Fisher Scientific (Pittsburgh, Pa.). Cremophor EL was purchased from Sigma-Aldrich (St. Louis, Mo.). Columbia Sheep's Blood agar plates (BA) and Human Blood Tween (HBT) Bilayer Medium were purchased from Becton Dickinson and Co. (Sparks, Md.). The *L. crispatus* (ATCC #33197), *L. iners* (ATCC #55195), and *G. vaginalis* (ATCC 14018) were purchased from ATCC (Manassas, Va.). The twin screw extruder was purchased from Thermo Fisher Scientific, (Tewksbury, Mass.). NANO 16 mm twin screw HME technology was purchased by Leistritz Corporation (Somerville, N.J.).

A variety of active pharmaceutical ingredients, which encompass a wide range of physicochemical characteristics, were chosen to demonstrate the versatility of the HME process. The panel of drug candidates selected for this example included both small and large molecule drug candidates that range in hydrophobicity. These molecules included dapivirine (small hydrophobic molecule), metronidazole (small hydrophilic molecule), levonorgestrel (hydrophobic molecule), griffithsin also known as GRFT (large molecule protein) and *Lactobacillus* bacteria (microorganism). These active pharmaceutical ingredients range in therapeutic application; from preventing HIV acquisition and transmission to treating sexually transmitted infections or maintaining vaginal microflora.

The vaginal films were manufactured using a twin screw HME method. All excipient powders and the active pharmaceutical ingredient were blended for 15 minutes using a bench top mixer to ensure content uniformity of the drug in the extrudate final product. The powder blend was transferred to the HME feeder to allow a controlled feeding rate. At the end of the extrusion, the product was collected by rolling the film sheet utilizing a chilled roll system. Once the film sheet was collected, it was cut using a die press into final unit doses and packed individually in aluminum foil pouches.

The puncture strength of extruded films was measured using a texture analyzer (TA.XT.PLUS™). The film was placed on the TA-108S5 fixture and was punctured by a ⅛ inch ball probe. The maximum force required to rupture the film was recorded. The following equation was used to calculate the puncture strength:

$$\text{Puncture strength} \left(\frac{g}{mm}\right) = \frac{\text{Force at break (g)}}{\text{Thickness of the film (mm)}}$$

Disintegration time was either measured visually or using a texture analyzer (TA.XT.PLUS™). For visual measurement, the film disintegration evaluation was conducted by submerging a film in 3 mL of Milli-Q water and mixing it using an orbital shaker. Visual assessment was conducted to monitor disintegration, which was measured as the time until complete film structural loss. For texture analyzer-based evaluation, 15 µL of Milli-Q water was added to the film once the TA probe came in contact with the film. The time until the probe breaks through the film was recorded as the disintegration time.

The residual water content of the films was measured using a Karl-Fisher apparatus (Metrohm, 758 KFD Titrino).

The drug release evaluation from the extruded film (dapivirine, metronidazole, and Griffithsin films) was conducted using Class IV USP apparatus flow-through dissolution system (SOTAX CE7 Smart, Sotax, Switzerland) equipped with auto-sampling and UV systems. These studies were conducted at 37° C. for 60 min with a flow rate of 16 mL/min.

The crystalline properties after the extrusion process were tested using a Mettler Toledo DSC 1 STARe System, equipped with a GC 200 gas controller. Approximately 4-8 mg of each sample (pure drug, physical mixture, and extruded film) were accurately weighed and placed in aluminum crucibles sealed with Mettler Toledo sealer. Analysis was conducted under a temperature range of 25° C. to 250° C. at a ramp rate of 10° C. per minute, using Na (50 mL/min) as the segment gas.

All results were presented as the mean±standard deviation (SD). Student's t test was used to compare the difference in mean values between the film data. Two-way ANOVA was used to compare the mean values of the stability values. P values <0.05 were considered statistically significant. Statistical analyses were conducted using GraphPad Prism software 6.07. The drug tissue concentrations were analyzed using student T-test for comparison of drug tissue concentrations post film exposure. P values <0.05 are considered statistically significant.

Example 1: Dapivirine Film

Dapivirine is (DPV) a small molecule, hydrophobic microbicide candidate with a logP of 5.27 at pH=9 (Akil, A et al. Development and Characterization of a Vaginal Film Containing Dapivirine, a Non-nucleoside Reverse Transcriptase Inhibitor (NNRTI), for prevention of HIV-1 sexual transmission, *Drug Deliv Transl Res*. 2011 Jun. 1; 1(3):209-222.). It is a potent, clinically-advanced HIV-1 replication inhibitor being developed as a topical microbicide candidate by the International Partnership for Microbicides (IPM). DPV is classified as a non-nucleoside reverse transcriptase inhibitor (NNTRI) with an $EC_{50}$ of 0.3 ng/mL and an $EC_{90}$ of 0.9 ng/mL against wild type and resistant mutant HIV (Hawes, S. E., et al., *Hydrogen peroxide-producing lactobacilli and acquisition of vaginal infections*. J. Infect. Dis., 1996, 174(5):1058-63). It binds with high affinity to the allosteric binding pocket on the reverse transcriptase enzyme near the catalytic site and inhibits HIV-1 replication. It has a high melting point of 220° C. and is not heat sensitive, and therefore can be utilized as a model hydrophobic molecule for the HME application. DPV has been formulated as an intravaginal ring (IVR), vaginal gel, and solvent casted film all of which have been tested in clinical trials (Bunge, K. E., et al., *A Phase 1 Trial to Assess the Safety, Acceptability, Pharmacokinetics, and Pharmacodynamics of a Novel Dapivirine Vaginal Film*. J. Acquir. Immune. Defic. Syndr., 2016, 71(5):498-505; Hawes, S. E., et al., *Hydrogen peroxide-producing lactobacilli and acquisition of vaginal infections*. J. Infect. Dis., 1996, 174(5): 1058-63).

Several DPV HME formulations were developed. One example is a DPV film formulation that contained 37.5% (w/w) POLYOX™ N80, 37.5% (w/w) KLUCEL™ Hydroxypropyl cellulose EF, 20.0% (w/w) Polyethylene glycol (PEG) 4000, 2.0% (w/w) PEG 400, and 2.0% (w/w) Vitamin E (acetate) and 1% DPV. The temperature of the extrusion was increased from 125° C. to 145° C. (Zone 1: 125° C.; Zone 2: 130° C., Zone 3: 135° C., Zone 4: 135° C.). The die melt was 145° C. The screw speed was 180 rpm. Film size was 1 inch×2 inches.

A high-performance liquid chromatography (HPLC) system (Dionex Ultimate 3000, Thermo Scientific) equipped with an auto-sampler, a quaternary pump, and a diode array detector was used to quantify DPV. This gradient method utilized a reversed phase chromatography using a C18 column (Acclaim 150×4.6 mm) at a wavelength of 290 nm. The mobile phase comprised 0.1% trifluoroacetic acid in water (v/v) and 0.1% trifluoroacetic acid in acetonitrile (v/v), at a flow rate of 1 mL/min. The mobile phase gradient was (minute; % B): 0; 30, 6.6; 46, 8.4; 46, 12.6; 54, 13.2; 80, 14.4; 80, 15; 30, 18; 30. The average retention time of DPV was approximately 10.3 min with lower limit of detection (LOD) of 0.025 μg/mL and lower limit of quantitation (LOQ) of 0.0825 μg/mL. Linearity of the detector response curve was at a range of 0.1 μg/mL to 100 μg/mL. Chromeleon software was used to capture data from the HPLC system.

The DPV film was off white, translucent and smooth. The average weight and thickness of the DPV film was 147.3±10.1 mg and 0.2±0.01 mm, respectively. DPV drug content was 1.3±0.1 mg/film with less than 2% water content present in the film. Puncture strength was 3.4±0.5 kg/mm Disintegration studies demonstrated a quick disintegration time of 46.64±8.05 seconds, which indicates the quick dissolving nature of the film. Dissolution (Cumulative Release after 15 minutes, %) was determined in 1% Cremophor using UV detection at 290 nm (using the UV system attached to the Sotax apparatus) and found to be 78.9±4.3. To determine crystallinity or amorphous state of DPV post extrusion, DSC analysis and microscopy images were utilized. Thermal analysis using DSC showed the thermal behavior of DPV before and after the extrusion process. A polymorphic transition of DPV drug substance was detected at 105° C. and the melting point at 220° C. No thermal endotherm peak was observed for DPV after the extrusion process. Microscope images confirm no crystals formed in the film post extrusion process.

*Lactobacillus* crispatus and *jensenii* (*L. crispatus* and *L. jensenii*), two *Lactobacillus* species present in the vagina, were used for the Standard Microbicide Safety Test (SMST) of the DPV films. Films were dissolved in overnight cultures of *L. crispatus* and *L. jensenii*. The suspension was incubated for 30 minutes at 37° C. and bacterial viability was determined. Viability samples were taken throughout incubation at time points 0 minutes and 30 minutes and determined by standard plate count. Compatibility of the film with the *Lactobacillus* was measured as log differences in bacterial viability. No loss of bacterial viability was observed after 30 minutes of incubation with the film. Thus, DPV did not hamper bacterial viability. A small fluctuation in bacterial viability observed after the exposure to the film product (Table 1). However, these changes were not significant since a log value must take place to be considered as a significant change in bacterial viability.

Table 1: Compatibility of the DPV Extruded film with *L. crispatus* and *L. jensenii*

The compatibility of the *Lactobacillus* was measured as the log difference in bacterial viability before and after exposure to the film product. No loss of bacterial viability was observed after 30 minutes of incubation with the film.

| Lactobacillus | Dapivirine Film (CFU) | Placebo Film (CFU) |
| --- | --- | --- |
| L. crisp ATCC 33197 | −0.138 | 0.011 |
| L. jen LBP 28AB | 0.168 | 0.005 |
| L. jen ATCC 25258 | 0.162 | 0.084 |

Anti-HIV activity testing was performed using a TZM-bl cell-based assay as previously described (Akil, A., et al., *Development and Characterization of a Vaginal Film Containing Dapivirine, a Non-nucleoside Reverse Transcriptase Inhibitor (NNRTI), for prevention of HIV-1 sexual transmission*. Drug Deliv. Transl. Res., 2011, 1(3):209-222). A DPV film was dissolved in 2 mL of saline and ten-fold serial dilutions were made. The DPV drug substance stock solution (1000 nM) was mixed in DMSO and serially diluted in DMEM with 10% BSA supplemented with antibiotics, which is the medium used in the TZM-bl assay. All dilution samples were added in triplicates to the TZM-bl cells that were plated. Afterward, HIV-1bal was added and cultured for 48 hours. The infection was detected by the addition of a chemiluminescent developer of luciferase, BrightGlo (Promega), to each well. For the background control and the maximal luciferase activity, cells alone and cells infected with HIV-1 were used respectively. The $IC_{50}$ was calculated using GraphPad Prism software (V6.0). For cellular toxicity evaluation, similar set up of the experiment was conducted. Except that for toxicity study, the cells were not exposed to the virus. In this study the cells were exposed to CellTiter-Glo, and luminescence signal was measured. Cellular viability was determined based on the deviation from the cell-only control (Nixon, B., et al., *Griffithsin protects mice from genital herpes by preventing cell-to-cell spread*. J. Virol., 2013, 87(11):6257-6269). The half maximal inhibitory concentration ($IC_{50}$) obtained for DPV HME film was 2 nM (FIG. 1). DPV substance had similar anti-HIV activity, while the placebo film had minimal but quantifiable anti-HIV activity due to the presence of the polymer in the film formulations. In addition, there was no loss in cellular viability due to the exposure of the cell to the DPV HME film. The cell viability remained greater than 80% throughout the assay.

To test the physical stability of DPV HME films, films were placed on stability at 25° C./65% relative humidity (RH) for 24 months and at 40° C./75% RH for 6 months. The films were tested at predetermined time points. At each time point, mass, thickness, appearance, microscopy, water content, puncture strength, disintegration, drug content, and dissolution were tested. In addition, *Lactobacillus* compatibility and in vitro anti-HIV activity (TZM-bl cell-based model) were tested at specific periods throughout the stability study. FIGS. 2A-2D depict film weight, drug content, dissolution, and puncture strength obtained from the stability study at the predetermined time points. In general, no significant change in film characterization and drug content occurred over time, when comparing the different time points to time zero. The water content of the film remained unchanged and below 2%. Furthermore, DPV anti-HIV activity in the HME film was maintained throughout the stability study at both conditions. Additionally, no cellular toxicity was observed at any time point, confirmed by the TZM-bl cellular assay. Finally, no loss of *Lactobacillus* viability was observed over the course of the stability study utilizing the SMST.

Figures 3A, 3B, 3C:
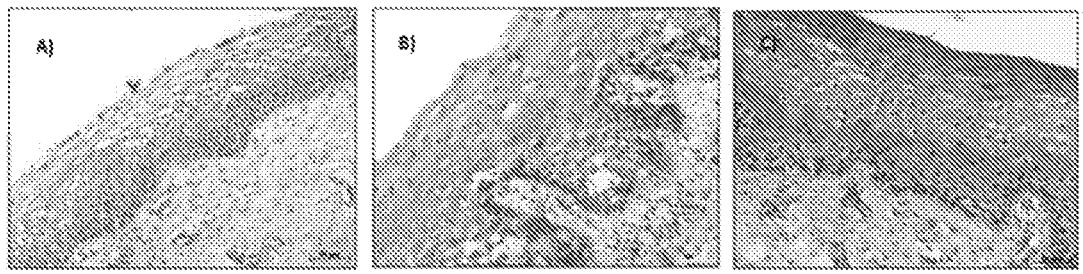
FIGS. 3A-3C show representative images of H&E staining of epithelium pre- and post-exposure to the solvent cast and hot melt extrusion films. The images are pre-exposed tissue to the film treatment (FIG. 3A), tissue exposed to solvent casted DPV film for 6 hours (FIG. 3B), and tissue exposed to HME DPV film for 6 hours (FIG. 3C). Hematoxylin was used to stain the nuclei of the cells in purple and the rest of the cell structures are colored red by the eosin stain. No significant changes in the tissue morphology were observed post-exposure to the films compared to the pre-exposed tissue.

The human ecto-cervical tissue was obtained from the University of Pittsburgh Health Sciences Tissue Bank as per approved IRB protocol PRO09110431. Tissue samples were collected from healthy volunteers undergoing routine hysterectomy. The tissue was prepared by removal of the excess stroma by a longitudinal slice through the specimen using a Thomas-Stadie Riggs tissue slicer. The thickness of the tissue was measured by a digital caliper. A section of the tissue was collected for histological evaluation to represent the pre-exposure state of the tissue. The tissue exposure studies were performed using an in-line-flow-through cell system. Epithelial tissue was placed within the flow-through system, with the epithelial layer faced towards the donor compartment. A 6 mm biopsy punch of DPV HME film or DPV solvent-casted film was dissolved in 450 μL of vaginal fluid stimulant (VFS) and placed in the donor compartment, on top of the tissue. The receptor medium, Dulbecco's Modified Eagle Medium (DMEM) was used for the receptor compartment, at a flow rate of 50 μL/min. The excised human ecto-cervical tissue was exposed to each film solution for 6 hours while the fraction collector collected receptor samples. To maintain biological temperature, the system was kept at 37° C. At the end of the 6 hour period of tissue to film exposure, the tissue was collected and cut into halves: one half was used for histological evaluation and the other half was used for the determination of DPV concentration by UHPLC. The results confirmed that DPV was present in the tissue after the exposure to both HME and solvent cast film Amount found in the tissue (µg/g): DPV HME Film 5.818±2.717, DPV SC Film 1.489±0.774). In addition, evaluations were conducted to determine the safety of DPV HME film to the epithelial layer of the vaginal canal. H&E stained tissue pre- and post-exposure are presented in FIGS. 3A-3C. The epithelial layer of the tissue was found to be intact and maintained structural integrity. No morphologic changes were detected after the exposure of the HME film and the solvent cast film to the tissue, when compared to the pre-exposed tissue.

All tissue (pre and post experiment) were individually placed in embedding cassettes and treated with formalin for 12-24 hours. Following formalin treatment, tissue cassettes were kept in 70% ethanol for at least 24 hours prior to processing. The tissue cassettes were then incubated in 95% ethanol for 1 hour, 100% ethanol for 1 hour (3 times), xylene for 1 hour (2 times), and paraffin for 3 hours. Using the embedding station (Lecia EG 1160), the tissue cassettes were embedded into paraffin blocks. Tissue blocks were sectioned at a thickness of 5 µm using a microtome (Olympus CUT 4060) and placed onto glass slides for staining.

Tissue safety evaluation was conducted using H&E staining After the permeability study, tissue processing, and paraffin embedding, Hematoxylin and Eosin were used. Morphological changes were evaluated using a microscope (Zeiss Axioskop 40) and imaged.

After the permeability assay, tissues were homogenized (Precellys 24 Homogenizer). The homogenized tissue was then subjected to liquid extraction. DPV was extracted from the homogenized tissue using acetonitrile, methanol, methyl-tert-butyl ether (MTBE), 25% $NH_4OH$ solution, 0.9% NaCl solution, and MilliQ water ($H_2O$). After liquid extraction samples were dried under nitrogen ($N_2$), they were reconstituted in an injection solvent containing (7:3 acetonitrile to water) for analysis. After sample preparation, samples were injected into a Waters Acquity ultra-high-performance liquid chromatography (UHPLC) system connected to a Thermo Quantum Access Advantage MAX triple quad mass spectrometer (with electric spray ionization source) for analysis. The method utilized a Phenomenex Hyperclone 3u BSD $C^8$ 150×4.6 mm column. The mobile phases comprised (A) 5 mM $NH_4FA$ Buffer in 60% acetonitrile and (B) 5 mM $NH_4FA$ Buffer in 80% acetonitrile. The injection volume was 40 µL and the run time was 6 minutes with a 1 mL/min flow rate. A positive SRM scan was used to monitor: 330.2 a158 for DPV and 334á145.1 for d4-DPV (internal standard). The range for the standard curve was 0.2-50 ng/mL and was determined to be linear (Akil, A., et al., *Development and Characterization of a Vaginal Film Containing Dapivirine, a Non-nucleoside Reverse Transcriptase Inhibitor (NNRTI), for prevention of HIV-1 sexual transmission*. Drug Deliv Transl Res, 2011, 1(3):209-222).

In sum, the DPV film showed that it could effectively inhibit the HIV-1 replication while maintaining the safety profile after the formulation process. The DPV film retained potent anti-HIV activity ($IC_{50}$=2 nM), similar to the DPV drug substance alone. These results confirmed that the DPV film formulation and the HME process did not affect the anti-HIV activity of DPV. The DPV film was tested for cellular toxicity and compatibility with *Lactobacillus*. The DPV film was found to be safe to the TZM-bl cells, human excised tissue and did not show harmful effects to *Lactobacillus*, a major component of the vaginal microflora, confirming that the safety profile was maintained. Taken together, these results confirm that HME is capable of manufacturing a highly effective and non-toxic DPV film.

Example 2: Metronidazole Film

Metronidazole is a hydrophilic (logP −0.46), heat stable (melting point 160.5° C.) small molecule that is commonly used as an antibiotic agent for the treatment of vaginal microbial infections. A metronidazole 0.75% vaginal gel is approved by the US Food and Drug Administration (FDA) as a treatment for bacterial vaginosis (BV) and is commercially available. Metronidazole diffuses passively into the cytoplasm of anaerobic bacteria, where it partially reduces cytoplasm proteins, such as ferrodoxin, which creates free radicals. The resultant free radicals interact with intracellular DNA, resulting in the inhibition of bacterial DNA synthesis and ultimately, bacterial death. Additionally, metronidazole was reported to have minimal antibiotic resistance (Austin, M., et al., *Microbiologic response to treatment of bacterial vaginosis with topical clindamycin or metronidazole*. J. Clin. Microbiol., 2005, 43(9):4492-4497). Taken together, metronidazole is the most common antibiotic prescribed for vaginal infections, such as BV, and is currently marketed for vaginal use as gel dosage form.

The metronidazole film formulation contained 56.25% (w/w) POLYOX™ N80, 15% (w/w) POLYOX™ N10, 2.25% (w/w) PEG 400, 1.5% (w/w) Vitamin E and 25% metronidazole. The temperature was increased from 110° C. to 120° C. The die melt was 125° C. The screw speed was 100 rpm. Film size was 1 inch×2 inches.

A high-performance liquid chromatography (HPLC) system (Waters Corporation; Milford, Calif.) equipped with an auto-sampler, a quaternary pump controller, and a diode array detector was used to quantify metronidazole. This isocratic method utilized a reversed phase chromatography using a C18 column (Zorbax Eclipse C18 4.6×100 mm) 150×4.6 mm) at a wavelength of 275 nm. The mobile phase comprised 0.1% trifluoroacetic acid in water (v/v) and 0.05% trifluoroacetic acid in acetonitrile (v/v), at a flow rate of 1 mL/min. Metronidazole was quantified by UV detection at 275 nm and the average retention time of metronidazole was approximately 2.5 minutes with 0.32 µg/mL for the lower limit of detection (LOD) and 1.056 µg/mL for lower limit of quantitation (LOQ). Linearity of the detector response curve was at a range of 1 µg/mL to 200 µg/mL. Empower software was used to capture the data generated by the HPLC system.

The metronidazole film was white, transparent, and smooth. The average weight and thickness of metronidazole film was recorded to be 205.8±14.2 mg and 0.2±0.02 mm, respectively. Metronidazole drug content was quantified via HPLC analysis and determined to be uniformly distributed, with total drug content being 50.0±4.5 mg/film. Additionally, the residual water present in the metronidazole film was found less than 1%. Puncture strength was 3.7±0.2 kg/mm. The disintegration analysis confirmed the quick (75.8±13.6 seconds) disintegration of the metronidazole film. Dissolution (Cumulative Release after 15 minutes, %) was determined in MilliQ water using sample collection and HPLC analysis and found to be 70.9±7.8.

To test the bioactivity of metronidazole film, *Gardnella vaginalis* (*G. vaginilis*) (ATCC 14018) was plated on HBT plates to form a lawn. A metronidazole film was placed in the middle of the plated bacteria and plates were incubated at 37° C. with 6% $CO_2$ for 48 hours. Post incubation, the plates were visually inspected for the formation of a zone of inhibition. Placebo films and metronidazole drug substance were prepared and tested in the same manner as the controls. The metronidazole film demonstrated a 1.5 cm zone of inhibition within the G. vaginilis lawn, which was comparable to the metronidazole drug substance's zone of inhibition. This confirms that G. vaginilis growth is inhibited by the presence of both the metronidazole drug substance alone and within the film. On the other hand, G. vaginilis was not affected by the placebo film.

In sum, metronidazole, a hydrophilic anti-microbial agent, was tested for bioactivity using a HBT plate containing a lawn of G. vaginalis. The metronidazole film demonstrated a zone of inhibition similar to the metronidazole drug substance. This test confirmed that metronidazole retained its antimicrobial activity after the HME process. This demonstrated that the hydrophilic small molecule metronidazole can be incorporated into the HME film while maintaining anti-microbial properties.

Example 3: Griffithsin Film

Griffithsin also known as GRFT, is an HIV entry inhibitor and a potent microbicide candidate. GRFT is a lectin that binds to mannose-rich glycans on the viral gp120 attachment protein of HIV to prevent infection. It is able to bind to the clusters of oligomannose N-Linked glycans on the HIV envelope protein gp120 (Chavoustie, S. E., et al., *Metronidazole vaginal gel 1.3% in the treatment of bacterial vaginosis: A dose-ranging study*. J. lower genital tract disease, 2015, 19(2):129-134). In addition, GRFT can inhibit the binding of HIV to Dendritic Cell-specific Intercellular adhesion molecule-3-Grabbing Non-integrin (DC-SIGN) receptor and thus, the resultant transfer of HIV-1 to CD4 target cells (Klein, C. E., et al., *The tablet formulation of lopinavir/ritonavir provides similar bioavailability to the soft-gelatin capsule formulation with less pharmacokinetic variability and diminished food effect*. JAIDS J. Acquir. Immune Defic. Synd., 2007, 44(4):401-410). GRFT is not only effective at HIV prevention, it also inhibits herpes simplex virus 2 (HSV-2) (Romano, J., et al., *Safety and availability of dapivirine (TMC120) delivered from an intravaginal ring*. AIDS research and human retroviruses, 2009, 25(5):483-488), hepatitis C virus (HCV) (D'Cruz, O. J. and F. M. Uckun, *Dawn of non-nucleoside inhibitor-based anti-HIV microbicides*. J. Antimicrobial Chemotherapy, 2006, 57(3):411-423), and severe acute respiratory syndrome coronavirus (SARS-CoV) (Nel, A., et al., *A safety and pharmacokinetic trial assessing delivery of dapivirine from a vaginal ring in healthy women*. AIDS, 2014, 28(10):1479-1487). GRFT is a small homodimer lectin that contains 121-amino acids with an approximate molecular mass of 12.7 kDa. It was identified in a genetic screen for antiviral activity and originally isolated from a red alga (*Griffithsia* sp.). Moreover, Kouokam et al, and O'Keefe et al, reported that GRFT was found to be safe to human cervical explants and in an in vivo rabbit model (Chavoustie, S. E., et al., *Metronidazole vaginal gel 1.3% in the treatment of bacterial vaginosis: A dose-ranging study*. J. lower genital tract disease, 2015, 19(2):129-134; Emau, P., et al., *Griffithsin, a potent HIV entry inhibitor, is an excellent candidate for anti-HIV microbicide*. J. medical primatology, 2007, 36(4-5):244-253).

GRFT solution was first lyophilized to remove the aqueous storage solution. The GRFT formulation contained 52.6% (w/w) POLYOX™ N80, 35.1% (w/w) PEG 4000, 8.8% (w/w) PEG 400, 3.5% (w/w) Vitamin E acetate, and 1% GRFT. The temperature was kept constant at 65° C. The die melt was 65° C. The screw speed was 100 rpm. Film size was 0.5×1.

The high-performance liquid chromatography (HPLC) system (Waters Corporation; Milford, Calif.) equipped with an auto-sampler, a quaternary pump controller, and a fluorescence detector, using an excitation wavelength of 273 nm, and an emission wavelength of 303 nm was used to quantify GRFT. The GRFT gradient was applied via a C18 column (Phenomenex Jupiter 5µ 300 Å 4.6×250 mm). The mobile phase comprised 0.1% trifluoroacetic acid in water (v/v) and 0.05% trifluoroacetic acid in acetonitrile (v/v) at a flow rate of 1 mL/min Gradient (time (min), B %): 0, 12%; 50, 20%; 16, 50%; 20, 12%; 50, 12%. The LOD found to be 0.3 µg/mL and the LOQ 1.0 µg/mL. Linearity of the detector response curve was at a range of 10 µg/mL to 500 µg/mL. Empower software was used to capture data from the HPLC system.

The GRFT film was clear, transparent, and smooth. The average weight and thickness of GRFT film was 129.4±25.9 and 0.1±0.01 mm, respectively. The total average drug content of GRFT in the film was 1.16±0.06 mg/film, less than 1% water content and disintegration time of 61.7±0.9 seconds. Puncture strength was 5.1±0.9 kg/mm Dissolution (Cumulative Release after 15 minutes, %) was determined in phosphate buffered saline using sample collection and HPLC analysis and found to be 57.7±6.3%.

To ensure that GRFT did not undergo fragmentation during the film manufacturing process sodium dodecyl sulfate polyacrylamide gel electrophoresis (SDS PAGE) was performed. The tested samples were GRFT powder post-lyophilization (before HME film manufacturing process), GRFT films, and GRFT drug substance. For this assay, BioRad precast Mini-PROTEAN™ TGX Any kD gels, BioRad Precision Plus, 1× Tris/Glycine/SDS Running buffer, and Protein Kaleidoscope Standards were utilized. GRFT samples were diluted to 1-8 µg of protein. 30 µL of these samples were combined with 30 µL of Laemmli sample loading buffer. Samples were boiled for 5 minutes following 5 minutes of cooling on ice. Each 30 µL sample contained 0.033 mg/mL-0267 mg/mL protein (according to the dilution level of the solution). In each well of the gel, 15 µL of sample was loaded and electrophoresed. Post electrophoresis, the detection of the protein was conducted by Coomassie Blue staining (Bio-Safe Coomassie Stain). Gel images were collected with a GEL DOC™ EZ System (Bio-Rad) (FIG. 4). GRFT post extrusion (see lanes 4 and 5) displayed bands between 10 kDa and 15 kDa. The GRFT control (lane 7) and lyophilized GRFT (lane 8) also displayed bands between 10 and 15 kDa. GRFT contains a 12.7 kDa monomer, which is visible on the gel and therefore confirms that the HME process did not affect the native GRFT structure. The banding pattern of GRFT between 10-15 kDa is common among proteins with similar molecular masses using this gel (BioRad precast Mini-PROTEAN™ TGX). The placebo extruded film (lanes 2 and 3) was run on the gel as negative control and did not show GRFT bands. Additionally, the binding ability of GRFT was evaluated using ELISA assay. GRFT maintained binding ability to gp120 binding pocket after the HME extrusion process.

Enzyme-linked immunosorbent assay (ELISA) was used to test the gp120 binding activity of the lyophilized GRFT (before HME film manufacturing process), GRFT films, and GRFT drug substance. The gp120 solution (HIV-1 gp120 CM was obtained through the NIH AIDS Reagent Program, Division of AIDS, NIAID, NIH (Cat #2968) was bound to a 96 well plate (Nunc MaxiSorp 96-well plates) overnight at 4° C. After overnight incubation at 4° C., the excess gp120 was removed and a blocking solution was added for two hours incubation at room temperature and washed. The various dilutions of GRFT samples were then added to a 96 well plate and incubated for one hour. The plate was then washed and primary goat anti-GRFT antibody was added and washed after one-hour incubation. The secondary antibody HRP-labeled rabbit anti-goat was added for one hour and washed. Tetramethyl-benzidine (TMB) substrate was applied to the wells for 3 minutes incubation, until the blue color was developed. To stop the reaction, sulfuric acid was added (yellow color). gp120 binding was detected at an optical density (OD) of 450 nm.

In sum, the selected large molecule protein GRFT, like most proteins, was known to be shear sensitive. It was predicted to be prone to degradation during the HME process. The GRFT film was tested for size (SDS-PAGE) and binding activity (ELISA) to confirm GRFT functionality post extrusion process. The GRFT was found to be intact and maintained its binding ability to the gp120 post HME processing. The GRFT was able to maintain its desired properties and function due to the relatively low temperature (65° C.) and modified screw speed (40-100 rpm) which allowed for minimal residence time of GRFT in the screw barrel during the extrusion process. The short residence time limited the exposure of GRFT to shear stress created during the HME process. In addition, since the formulation components comprised a thermoplastic polymer, GRFT was protected during the extrusion process. This example demonstrated that the GRFT maintained its structure and functionality. Therefore, it can be concluded that the HME can be used for the manufacturing film containing large molecules protein such as GRFT.

Example 4: *Lactobacillus* Film

*Lactobacillus* species are the predominant bacteria that comprise the vaginal microflora. They play an important role in the healthy balance of the vaginal micro-environment. These bacteria suppress the growth of harmful pathogenic bacteria in the vagina through competitive inhibition and provide protection from various pathogens due to the production of lactic acid and hydrogen peroxide ($H_2O_2$). The lactic acid produced by *Lactobacillus*, a by-product of the metabolism of glycogen released by vaginal epithelial cells, allows the vaginal fluid to remain acidic (healthy vaginal pH 3.5-4.7). The lactic acid and low pH of the vaginal fluid create a selective antimicrobial barrier against harmful pathogens that can cause vaginal infections such as BV (Valore, E. V., et al., *Antimicrobial components of vaginal fluid*. Am. J. Obstet. Gynecol., 2002, 187(3):561-8). Furthermore, $H_2O_2$, produced by specific *Lactobacillus* species, maintains a healthy vaginal environment due to its toxicity to nonresident pathogenic microorganisms (Eschenbach, D. A., et al., *Prevalence of hydrogen peroxide producing Lactobacillus* species *in normal women* and *women with bacterial vaginosis*. J. Clin. Microbiol., 1989, 27(2):251-6; Eschenbach, D., *Treatment of pelvic inflammatory disease*. Clin. Infect. Dis., 2007, 44(7):961-3). Additionally, *Lactobacillus* is known to produce powerful antimicrobial proteins, such as bacitracin. These antimicrobial proteins disrupt the cell wall and peptidoglycan synthesis of Gram positive and Gram negative bacteria leading inhibition of harmful pathogens (Klaenhammer, T. R., *Bacteriocins of lactic acid bacteria*. Biochimie, 1988, 70(3):337-49).

*Lactobacillus*-containing products can be applied locally in order to maintain vaginal colonization of $H_2O_2$-producing *Lactobacillus* and can be defined as probiotic products (Eschenbach, D., *Treatment of pelvic inflammatory disease*. Clin. Infect. Dis., 2007, 44(7):961-3). Probiotics are live microorganisms that offer benefits when administered to the host (Consultation, F.a.A.O.a.W.H.O.E., *Health and Nutritional Properties of Probiotics in Food including Powder Milk with Live Lactic Acid Bacteria*. Food and Agriculture Organization of the United Nations and World Health Organization, 2001:1-34). Vaginal probiotics may be composed of one or multiple species of *Lactobacillus*.

The *Lactobacillus* film formulation contained 50.85% (w/w) POLYOX™ N10, 33.90% (w/w) PEG 4000, 8.47% (w/w) PEG 400, 3.39% (w/w) vitamin E, and 3.39% bacterial-load. The temperature was kept constant at 65° C. The die melt was 65° C. The screw speed was 40 rpm. Film size was 0.5 inch×1 inch.

Columbia agar with 5% sheep blood (Becton Dickinson and Co., Sparks, Md.) was used to evaluate the bacterial viability. Bacteria-loaded films were dissolved in sterile 1× phosphate-buffered saline (PBS) and serial dilutions were performed. Each of the dilutions were plated onto agar plates and incubated at 37° C. with 6% $CO_2$ for 48 hours. After incubation the period the bacteria colony forming units (CFU) were counted and recorded.

An assay utilizing the flow cytometry LSRII (BD Biosciences) was developed. *Lactobacillus* was separated from the film particles based on the size and granularity. A film was submerged into a mixture of MilliQ $H_2O$ and 1 mL sheath fluid (BD Biosciences) and samples were collected for analysis at predetermined time points. These samples were analyzed by the flow cytometry LSRII with the forward scatter (FSC) and side scatter (SSC) parameters turned on. FSC correlates with cell size and SSC correlates with the granularity of the samples.

The film was clear, transparent and smooth. The average weight and thickness of the bacterial-loaded film was 133.9±8.7 mg and 0.1±0.008 mm, respectively. The bacteria colonies were uniformly distributed throughout the film and the bacterial CFUs were found to be $10^7$. The water content present in the bacterial film was found to be less than 1%. The disintegration time of the film was recorded to be 64.2±0.3 seconds. Puncture strength was 5.1±0.9 kg/mm. The results from the dissolution evaluation suggested that the release of the bacteria from the film increased in a time dependent manner. The peak bacterial release was observed after 30 minutes in contact with the aqueous environment (FIGS. 5A-5C). In addition, the viability of the bacteria was monitored during the dissolution assay and viability was confirmed throughout the experiment.

Hydrogen peroxide detection was determined using a Tetramethyl-benzidine (TMB) plate. Bacteria-loaded films were dissolved in sterile 1×PBS. The film solutions were placed on TMB plates. The plates were placed in an anaerobic box at 37° C. for 48 hours. The plates were then exposed to air. The horseradish peroxidase present in TMB plate oxidizes TMB in the presence of hydrogen peroxide produced by the *Lactobacillus* to form a blue pigment (Eschenbach, D. A., et al., *Prevalence of hydrogen peroxide-producing Lactobacillus* species *in normal women* and *women with bacterial vaginosis*. J. Clin. Microbiol., 1989, 27(2): 251-6). The presence of blue color confirms $H_2O_2$ production by *Lactobacillus* and was visually compared to positive and negative controls. The *L. crispatus* (ATCC #33197) is a positive control for this test since it known for the ability of hydrogen peroxide production while *L. iners* (ATCC #55195), is a negative control since it does not produce hydrogen peroxide. Post incubation and upon exposure to the air, the plate shows the *Lactobacillus* from the HME film produced a blue color present in the zone of growth similar to the *L. crispatus* positive control zone. On the other hand, no blue color was produced in the zone of *L. iners* growth. Therefore, it can be concluded that the *Lactobacillus* retained the ability to produce hydrogen peroxide post extrusion.

Litmus milk (BD, B11343) assay was used for the detection of lactic acid production. Bacteria-loaded films were evaluated for lactic acid production. Film was dissolved in a 5 mL litmus milk sterile solution and incubated at 37° C. with 6% $CO_2$ for 48 hours. Litmus milk-bacterial solutions were visually inspected for color change. The litmus milk changed from a purple color to a whitish color with the production of lactic acid. The color change was recorded as (+) for color change and (−) for no change. The results from a litmus milk assay performed after the film manufacturing process showed a decrease in pH, which confirmed that the bacteria produced lactic acid after release from the film. Both the HME bacterial-loaded film and the control sample were assigned (+) for color change and the litmus milk negative control was assigned (−).

In sum, the production of bacteria loaded film was thought to be challenging since bacteria are sensitive to environmental changes such as exposure to high heat and shear. In this example, the HME process was modified to minimize heat and shear exposure to the bacteria. Bacteria contained in the films were able to maintain viability and produce both hydrogen peroxide and lactic acid following the extrusion process, confirming that bacterial-loaded films can be produced by HME manufacturing process Examples 1-4 Summary The drug dissolution test confirmed that within one hour, all four of the active pharmaceutical ingredients of Examples 1-4 were released from the film. More specifically, for each film, over 50% of all the total active agent was released from the film within the first 10 minutes of the test. The rapid drug release can be attributed to the film forming polymer, PEO, and the presence of PEG4000, which is a strong disintegration agent. The rapid release allows the active pharmaceutical ingredients to reach the vaginal canal within minutes from the time that the film is administered, ensuring rapid availability to achieve the therapeutic effect.

All the HME films were evaluated for the water content present in the film. In all the films, except the DPV film, water content was found to be less than 1%. The water content of the DPV film was less than 2%. In both cases the water content is considered to be low. The low residual water in the films was due to the total lack of water in the formulation. HME is a "dry" process and therefore, low residual water was expected. The slightly higher water content present in the DPV film (2%) could be a result of the HPC in the formulation. HPC is a hygroscopic polymer that can absorb moisture from the air during the manufacturing process. The water content found in the film is considered to be low compared to other films manufactured by solvent cast (Akil, A., et al., *Formulation and characterization of polymeric films containing combinations of antiretrovirals (ARVs) for HIV prevention*. Pharm. Res., 2015, 32(2):458-68). This is a desirable attribute for the formulation because the amount of water in the film can have an impact on the film structural stability over time and is helpful to minimize microbial growth.

Example 5: Multilayered Metronidazole and *Lactobacillus* Film

Metronidazole vaginal film was produced using a NANO 16 mm twin screw HME technology made by Leistritz Corporation (Somerville, N.J.). The metronidazole was mixed with 45% (w/w) POLYOX™ N80, 26.3% (w/w) POLYOX™ N10, 2.25% (w/w) PEG 400, and 1.5% (w/w) Vitamin E acetate and 25% metronidazole. At the end of the extrusion process, the product was collected using a system capable of rolling and cooling the film sheet extrudate.

Bacteria-loaded film was manufactured using a twin screw HME. The film forming polymer, PEO (50.85% (w/w)), was mixed with 33.90% (w IN) PEG4000, 8.4% (w/w) PEG 400 as well as 3.39% (w/w) antioxidant Vitamin E. 3.39% *L. jensenii*, bacterial powder was added to the mixture and subsequently transferred to the HME hopper. The extruder was set to 60° C. and the screw mixing speed was set to 40 rpm. After extrusion, the metronidazole film was placed at the end of the die to allow the bacteria-loaded film to be extruded directly on top of it. As the soft bacterial film extrudate was allowed to harden, the two films became fused into the final multilayer form. Once the film sheet was cooled, it was hand cut into 0.5 inch×1 inch. Each film unit dose was then packed individually and sealed.

Metronidazole was analyzed and quantified utilizing a high-performance liquid chromatography (HPLC) system (Waters Corporation; Milford, Calif.) equipped with an auto-sampler (model 717plus), a quaternary pump controller (model 600), and a diode array detector. This method utilized a reversed phase chromatography using a C18 column (Zorbax Eclipse C18 4.6×100 mm) 150×4.6 mm) at a wavelength of 275 nm at a retention time of 2.5 minutes. This isocratic method used mobile phases comprised 0.1% trifluoroacetic acid in water (v/v) and 0.05% trifluoroacetic acid in acetonitrile (v/v), at a flow rate of 1 mL/min. Linearity of the detector response curve was at a range of 1 µg/mL to 200 µg/mL with 0.32 µg/mL for the lower limit of detection (LOD).

The multilayer film was smooth, soft, white, and translucent. The bacterial uniformity and concentration ($10^7$ CFU) remained the same as in the single layer bacteria film ($10^7$ CFU) as well as in the metronidazole multilayer film. The combination film's water content was less than 1% and the puncture strength (5.5±0.5 kg/mm) was also similar to the single layer film. The mass and thickness, however, were almost doubled, at 238.0±47.9 mg and 0.3±0.03 mm, respectively. This increased mass and thickness was expected since combination film contains two film layers.

Evaluation of bacterial viability, colonization and uniformity was conducted utilizing Columbia Sheep's Blood agar plates (BA). Bacteria-loaded film combinations were dissolved in sterile PBS and serial dilutions were performed. Each of the dilutions was plated onto BA plates and incubated at 37° C. with 6% $CO_2$ for 48 hours. The colony forming units from each dilution were counted and reported. Bacterial powder (before HME) was evaluated for viability and colonization as a control.

To test the bioactivity of bacterial/metronidazole combination film, *G. vaginalis* (ATCC 14018) was plated on Human Blood Tween Bilayer (HBT) plates to form a lawn. Bacteria/metronidazole film was placed in the middle of the HBT plated bacteria and plates were incubated at 37° C.

with 6% $CO_2$ for 48 hours. Post incubation, the plates were visually inspected for the formation of a zone of inhibition and *L. jensenii* growth. Placebo films, metronidazole drug substance, and bacterial loaded film were prepared and tested in the same manner as the controls. The combination film demonstrated a 1.5 cm zone of inhibition within the *G. vaginalis* lawn, comparable to the metronidazole only film zone of inhibition. The placebo film did not demonstrate any inhibition properties. Additionally, the bacteria were released from the combination films and able to colonize within the zone of inhibition created by the metronidazole. Therefore, the desired in vivo antimicrobial and probiotic effects of the combination film were confirmed in vitro. After the bioactivity of the combination film was confirmed, the bacteria that grew within the metronidazole-induced zone of inhibition were swabbed from the HBT plate. The bacterial-swab was transferred to litmus milk and a TMB plate, for lactic acid and hydrogen peroxide evaluation, respectively.

Litmus milk assay was used for the detection of lactic acid production. Bacteria/metronidazole combination film, placebo film and as a control, and *L. crispatus* (ATCC #33197) were placed in 5 mL sterile litmus milk solution in individual vials. Each vial was placed at 37° C. with 6% $CO_2$ for 48 hours. Litmus milk solutions were visually inspected for color change. The litmus milk changed from a purple color to a pink color with the production of lactic acid. Litmus milk contains Litmus, which is a colorimetric pH indicator that appears purple at neutral pH and pink under acidic condition. It also contains bacteria metabolized molecule including milk sugar, lactose, and milk protein, casein. When the lactose is fermented by lactic acid producing bacteria such as the *Lactobacillus* species, the litmus will change in color from purple to pink because lactic acid is acidic compound which reduce the pH in the litmus milk solution. The color change was recorded as (+) for color change and (−) for no change. The results from the litmus milk assay (post HME process and post exposure to both metronidazole and *G. vaginalis*) showed a decrease in pH. The color of the litmus milk changed from purple to pink, which indicates lactic acid production. Both the HME combination film and the control sample were assigned (+) for color change, and the litmus milk negative control was assigned (−). This color change confirms that the bacteria produced lactic acid after release from the film and after exposure to metronidazole and *G. vaginalis*. Since higher vaginal pH is associated with increased susceptibility to vaginal infections, such as BV, the low pH maintained by the lactic acid production post release from the film is a fundamental requirement for a probiotic vaginal product.

Hydrogen peroxide detection was determined using a Tetramethyl-benzidine (TMB) plate. Bacteria powder and bacteria/metronidazole film were tested using the same method. The plates were placed in an anaerobic box at 37° C. for 48 hours. The plates were then exposed to air. The horseradish peroxidase present in TMB plate oxidizes TMB in the presence of hydrogen peroxide produced by the lactobacilli to form a blue pigment (Eschenbach, D. A., et al., *Prevalence of hydrogen peroxide-producing Lactobacillus species in normal women and women with bacterial vaginosis*. J. Clin. Microbiol., 1989, 27(2):251-6). The presence of blue color was visually compared to positive and negative controls. The *L. crispatus* (ATCC #33197) served as a positive control for this test, because of its ability to produce hydrogen peroxide, while *L. iners* (ATCC #55195) served as a negative control, due to its lack of hydrogen peroxide production. Blue color was detected on the TMB plate post incubation and exposure to air. The blue color was compared to the blue color present in the zone of growth and was similar to the *L. crispatus* positive control zone. On the contrary no blue color was produced in the zone of *L. iners* growth. The results suggested that the *Lactobacillus* from the HME combination film retained the ability to produce hydrogen peroxide post extrusion and post exposure to the metronidazole.

Bacteria loaded film samples were analyzed by a LSRII (BD Biosciences) flow cytometer with the forward scatter (FSC) and side scatter (SSC) parameters on. This method allows the separation of bacteria from the film formulation based on the size and granularity of the bacteria. A film was suspended in a mixture of sterile MilliQ water and Sheath buffer (BD Biosciences) (3:1 ratio). Samples were constantly and gently mixed throughout the experiment. 200 μL of the samples were collected at the following time intervals: 0, 15, 30, 45, 60, 75, 90, and 105 minutes and tested using flow cytometry. After removing each sample at each time point from the vessel, 200 μL of dissolution media was added to allow constant total volume in the system.

Metronidazole dissolution assay was conducted using class IV USP flow-through dissolution system (SOTAX CE7 smart, Sotax Switzerland) connected to an auto sampler with 16 m/min flow rate. The assay was conducted at 37° C. for 60 minutes. At predominant time interval, samples were collected and analyzed using HPLC assay. The bacterial peak release was detected after 30 minutes, starting when the film came in contact with the dissolution media. This quick release is similar to the results observed in the single layer film. Likewise, 70% of the metronidazole was released within the first 15 minutes of the dissolution test.

Bacteria/metronidazole HME combination films were found to be uniform and viable. The bacterial CFU from the combination film was similar to the CFU found in the bacteria powder (pre HME process) and bacteria-only film ($10^7$ CFU). The retained viability and uniformity confirm that HME can be utilized for production of a Bacteria-loaded vaginal film and combination film of antibiotic and probiotic.

Example 6: Multicomponent Dapivirine and Levonorgestrel Film

In this example, a hot melt extrusion (HME) manufacturing method was utilized for the development of a single layer combination film and multilayer combination film formulation for the simultaneous delivery of two pharmaceutical agents—dapivirine (DPV) and levonorgestrel (LNG). A single layer combination vaginal film comprises the two active pharmaceutical ingredients in one film layer. A multilayer combination vaginal film contains each active pharmaceutical ingredient in non-intersecting, separate layers that are combined into one film. DPV is a potent non-nucleoside reverse transcriptase inhibitor (NNRTI) of HIV and LNG is a synthetic female sex hormone (progesterone) that promotes contraception.

DPV, LNG, and LNG/DPV single layer film were manufactured using the same method. The LNG/DPV combination film, on the other hand, was manufactured in a two-step process due to unavailable access to two twin screw HMEs for co-extrusion process. All films were manufactured utilizing a twin-screw NANO 16 Leistritz extruder. DPV, LNG, and LNG/DPV combination film prototypes were composed of 37.0% (w/w) POLYOX™ N80, 37.0% (w/w) HPC KLUCEL™ EF, 20.0% (w/w) PEG 4000, 2.0% (w/w) PEG 400, 2.0% (w/w) vitamin E acetate, 1.0% (w/w) DPV, and 1.0%

(w/w) LNG. In general, all excipients and active pharmaceutical ingredients were blended using a bench top mixer. The powder blend was transferred to the K-tron feeder, which is connected to the twin screw extruder., the screws to 180 rpm, and the barrel temperature to increase from the lowest temperature (115° C.) at the feeding zone to the highest temperature (140° C.) at the die. For the multilayer LNG/DPV film, the DPV film layer was manufactured first followed by LNG film manufacturing as a secondary layer to create two-layer films. The process used to develop the multilayer film required a sequential co-HME procedure. This process yielded a multilayer film containing one layer of the DPV formulation and one layer containing the LNG formulation. All films were off white, translucent, flexible and smooth.

A high-performance liquid chromatography (HPLC) system (Dionex Ultimate 3000, Thermo Scientific), equipped with an auto-sampler, quaternary pump, and diode array detector, was used to quantify DPV, LNG, and combination LNG/DPV in the film. To analyze the DPV film, a reversed phase chromatography method using a C18 column (acclaim 150×4.6 mm) was utilized, detected at a wavelength of 290 nm. The mobile phase comprised (A) 0.1% trifluoroacetic acid in water (v/v) and (B) 0.1% trifluoroacetic acid in acetonitrile (v/v), at a flow rate of 1 mL/min. The mobile phase gradient was (minute, % B): 0; 30, 6.6; 46, 8.4; 46, 12.6; 54, 13.2; 80, 14.4; 80, 15; 30, 18; 30. The LOD for this assay was 0.025 µg/mL and the LOQ was 0.0825 µg/mL.

To analyze LNG, reversed phase chromatography using a C18 column (acclaim 150×4.6 mm) was utilized, detected at a wavelength of 244 nm with LOD of 0.015 µg/mL and LOQ of 0.0495 µg/mL. The mobile phases comprised (A) water and (B) acetonitrile, at a flow rate of 1.5 ml/min. The mobile phase gradient was (minute, % B): 0, 40.0; 8.2, 60.0; 9.0, 80.0; 16.0, 60.

Film samples (LNG and DPV from the single entity film) were weighed and dissolved in 50% acetonitrile, followed by vortexing at 1000 rpm until the films were completely dissolved. These samples were then centrifuged at 10,000 rpm for 10 minutes. The supernatant of all the samples was filtered using a 0.22 µm PTFE filter to remove polymer debris. The DPV and LNG drug content present in the film was detected using an appropriately designed HPLC analysis assay, as described above. The drug concentration of the film samples was calculated by measuring the peak area of the sample and comparing it to the peak area of a calibration curve with $R^2=0.999$.

The average weight and thickness of the LNG only film was 185.1±11.1 mg and 160.0±18.0 µm, respectively. LNG drug content was 1.7±0.2 mg/film and the water content (%) present in the film was 0.97±0.05. Disintegration studies demonstrated a quick disintegration time of 82.30±16.53 seconds, which indicates the quick dissolving nature of the film. The DPV only film, average mass and thickness was 147±10.1 mg and 158.0±10.0 µm, respectively. DPV drug content was 1.3±0.1 mg/film, water content was 2.0%, puncture strength of 3.43±0.47 kg/mm and disintegration time of 46.6±8.1 seconds. The two films were manufactured using the same HME process condition and the same formulation and therefore, the films have similar characteristics.

The combination LNG/DPV single layer film found to have average mass of 163.8±13.9 mg and average of 156.7±28.2 µm thick. The DPV and LNG content found to be 1.4±0.1 and 1.5±0.1 mg/film, respectively. The water content remained low at 1.3±0.1(%), with a puncture strength of 3.5±0.5 kg/mm and a disintegration time of 62.5±7.8 seconds. The single layer film characteristics are similar to the single entity films, which indicates that the combination of the active pharmaceutical ingredients in the single layer film did not have a significant effect on the film platform.

The multilayer combination film had an average mass of 335.4±20.3 mg and average thickness of 338.9±39.8 µm. The film mass and thickness are significant higher compared to the single layer film. This is because the film contained two layers of films in one platform. The drug content was found to be similar to the single layer film and to the single entity films (DPV 1.3±0.2 mg/film and LNG 1.7±0.2 mg/film). Water content and puncture strength were 1.2±0.1% and 3.8±0.4 kg/mm, respectively, which are similar to the single layer combination film and the single entity films. The multilayer disintegration time was not as quick as the single layer and found to be 237.2±68.2 seconds. The longer disintegration time is due to the two layers of the film. The water and the probe used in this assay, need to penetrate through a much thicker film and therefore it is reported to have longer disintegration time.

Figure 6A:
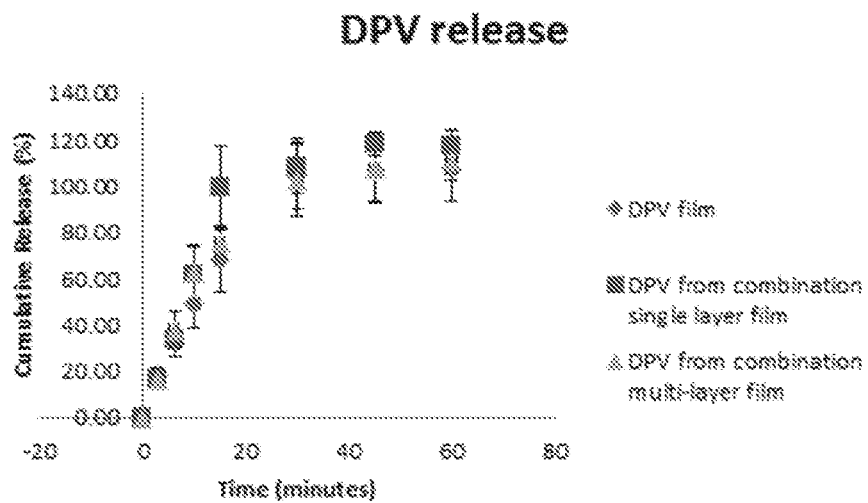
FIGS. 6A-6B show the dissolution profiles of LNG, DPV, and combination films.
Figure 6B:
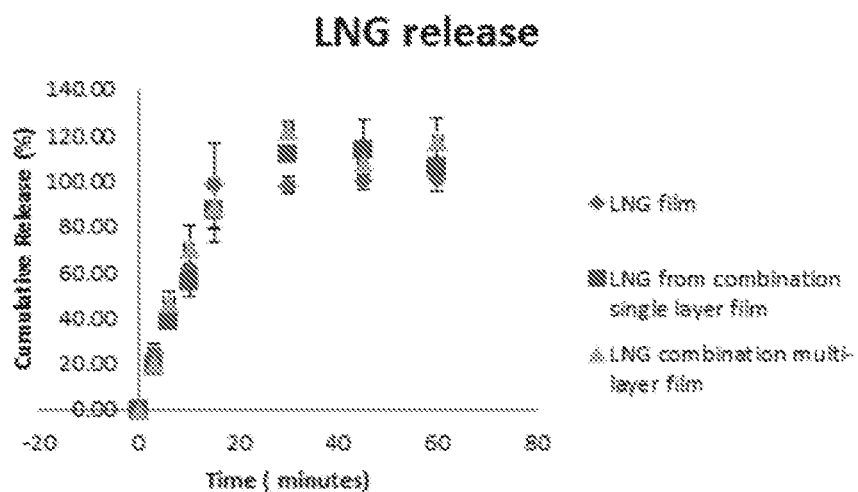

A dissolution assay was conducted using a Class IV USP apparatus (SOTAX CP7 smart, Sotax, Switzerland) with a flow rate of 16 mL/min. The dissolution media was 40% acetonitrile in distilled water, which met the sink condition of both DPV and LNG. The studies were conducted at 37° C. for 60 min, with sampling at appropriate time intervals. At predetermined time intervals, a 500 µL aliquot, was transferred to be analyzed using HPLC for drug content. The assay showed that DPV and LNG were released from the films within 20 minutes; from the time the films were first exposed to the dissolution media. The LNG and DPV release profiles were not affected by the presence of each other (FIGS. 6A-6B). This result was consistent in all 4 films: the single entity film and LNG/DPV combination film (single and multi-layer film).

Figure 7:
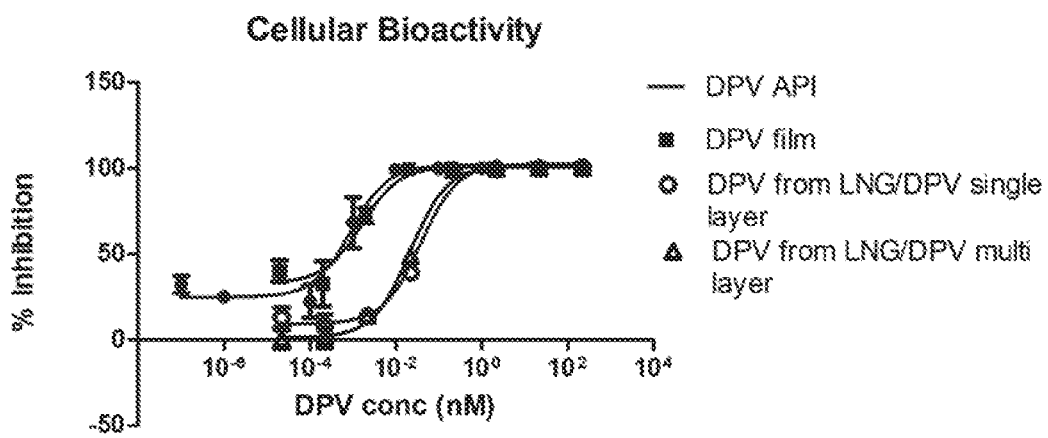
FIG. 7 shows the in vitro assessment of anti-HIV activity of DPV drug substance, single entity HME film, and combination HME films (single and multilayer) in TZM-bl cellular assay. DPV from the combination HME film maintained larger $IC_{50}$ compared to the DPV drug substance after the formulation and extrusion process.

Anti-HIV activity testing was performed using a TZM-bl cell-based assay. A 1 inch×2 inches DPV, LNG, combination LNG/DPV, or placebo film were dissolved in 2 mL of saline and ten-fold serial dilutions were made. DPV and LNG drug substances were used as controls. The DPV and LNG drug substance stock solutions (1000 nM) were mixed in DMSO and serially diluted up to $10^7$ in DMEM with 10% BSA supplemented with antibiotics, which is the medium used in the TZM-bl assay. All dilution samples were added in triplicate to plated TZM-bl cells. Afterwards, HIV-1$_{bal}$ was added and cultured for 48 hours. The infection was detected by the addition of a chemiluminescent developer of luciferase, BrightGlo (Promega), to each well. For the background control and the maximum luciferase activity, cells alone and cells infected with HIV-1 were used, respectively. The IC$s_{50}$ was calculated using GraphPad Prism software (V6.0) (Nixon, B., et al., *Griffithsin protects mice from genital herpes by preventing cell-to-cell spread.* J. Virol., 2013, 87(11):6257-6269). The DPV single entity film demonstrated similar bioactivity to the DPV drug substance, therefore, it can be concluded that the HME process did not affect the DPV bioactivity. The IC$s_{50}$ of DPV from the combination single layer film was found to be similar to the DPV from the multilayer combination film (see FIG. 7). This result suggests the decreased DPV IC$s_{50}$ was caused by the presence of LNG in the formulation. Furthermore, the in vitro cellular assay showed no cellular toxicity of the HME film, placebo film, and DPV drug substance.

*Lactobacillus* crispatus and *jensenii* were used for the Standard Microbicide Safety Test (SMST) of the DPV, LNG and combination LNG/DPV films Films were dissolved in a bacterial suspension and incubated for 30 min at 37° C., and viability was determined by standard plate count. Compatibility of the film with the Lactobacilli was measured as the Log difference in bacterial viability (from T=0 min to T=30 min). The *Lactobacillus* tested in this assay were unaffected by the exposure to the film products. To be considered "unsafe", the loss in viability must decrease by a log difference. Results showed that all four films are non-toxic to the *Lactobacillus* strains, and therefore, no loss of bacterial viability was observed.

To test the physical stability of DPV, LNG, and combination HME films, the films were stored at 25° C./65% relative humidity (RH) for 24 months and at 40° C./75% RH for 6 months. The films were tested at predetermined time points. At each time point, mass, thickness, appearance, microscopic appearance, water content, puncture strength, disintegration, drug content, and dissolution were tested. In addition, *Lactobacillus* compatibility and in vitro anti-HIV activity (TZM-bl cell-based model) were tested at specific periods throughout the stability study. The films were found to be stable at both conditions.

Human ecto-cervical tissue samples, collected from healthy volunteers undergoing routine hysterectomy, were obtained from the University of Pittsburgh Health Sciences Tissue Bank as per approved IRB protocol PRO09110431. The tissue was prepared by removal of excess stroma via a longitudinal slice using a Thomas-Stadie Riggs tissue slicer. The thickness of the tissue was measured by a digital caliper. A section of the prepared tissue was collected and labeled as "PRE-tissue" for later histological evaluation. The tissue permeability studies were performed using an in-line flow-through diffusion cell system. Tissue specimens were placed within the flow-through system, with the epithelial layer faced towards the donor compartment. A 6 mm biopsy punch of film was dissolved in 450 µL of vaginal fluid stimulant (VFS) and placed in the donor compartment, on top of the tissue. The receptor medium, Dulbecco's Modified Eagle Medium (DMEM), was used for the permeability assessment, at a flow rate of 50 µL/min. The excised human ecto-cervical tissue was exposed to each film solution for 6 hours while the fraction collector (Gilson) collected receptor samples. In order to maintain biological temperature, the system was kept at 37° C. with circulating heated water. At the end of the 6 hour, the tissue was collected and cut into halves: one half was used for histological evaluation and the other half was used for the determination of DPV and LNG concentration by UHPLC-mass spectrometry analysis. The results confirmed that DPV was present in the tissue after the exposure of the films to the tissue (DPV HME film: 0.0426±0.0282; DPV single layer film: 0.0542±0.0533; DPV multilayer film: 0.0125±0.0167). This is an indication that the co-delivery of DPV and LNG did not impact the permeability of DPV to the tissue.

All tissue (pre and post experiment) were individually placed in embedding cassettes and treated with formalin for 12-24 hours. Following formalin treatment, tissue cassettes were kept in 70% ethanol for at least 24 hours prior to processing. The tissue cassettes were then incubated in 95% ethanol for 1 hour, 100% ethanol for 1 hour (3 times), xylene for 1 hour (2 times), and paraffin for 3 hours. Using an embedding station (Lecia EG 1160), the tissue cassettes were embedded into paraffin blocks. Tissue blocks were sectioned at a thickness of 5 µm using a microtome (Olympus CUT 4060) and placed onto glass slides for staining.

H&E staining was conducted to detect any gross morphological changes in tissue structure as a result of exposure to the product. After the tissue exposure period, tissue was processed and embedded in paraffin, Hematoxylin and Eosin were used to stain the tissue nuclei and cell components, respectively. Morphological changes were evaluated using a light microscope (Zeiss Axioskop 40) and imaged. The epithelial layer of all exposed tissues remained intact and maintained structural integrity. No morphologic changes were detected after the exposure of the HME films the tissue, when compared to the pre-exposed tissue.

After the permeability assay, tissues were homogenized (Precellys 24 Homogenizer). The homogenized tissue was then subjected to liquid extraction. DPV and LNG were extracted from the homogenized tissue using acetonitrile, methanol, methyl-tert-butyl ether (MTBE), 25% ammonium hydroxide ($NH_4OH$) solution, 0.9% sodium chloride (NaCl) solution, and MilliQ water. After liquid extraction, samples were dried under nitrogen ($N_2$) and reconstituted in 30% acetonitrile injection solvent for analysis. After sample preparation, samples were injected into a Waters Acquity ultra-high-performance liquid chromatography (UHPLC) system connected to a Thermo Quantum Access Advantage MAX triple quad mass spectrometer (with electric spray ionization source) for analysis. The method utilized a Phenomenex Hyperclone 3u BSD C8 150×4.6 mm column. The mobile phases comprised (A) 5 mM ammonium formate ($NH_4FA$) buffer: acetonitrile (40:60) (B) 5 mM $NH_4FA$ buffer: acetonitrile (20:80) with a 1 mL/min flow rate (Akil, A., et al., *Development and Characterization of a Vaginal Film Containing Dapivirine, a Non-nucleoside Reverse Transcriptase Inhibitor (NNRTI), for prevention of HIV-1 sexual transmission*. Drug Deliv. Transl. Res., 2011, 1(3): 209-222).

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

Example 7: Multilayer Metronidazole and Clotrimazole Film

In this example, a hot melt extrusion (HME) manufacturing method was utilized for the development of a multilayer combination film formulation for the simultaneous incorporation of physicochemically diverse pharmaceutical agents—hydrophilic metronidazole (MTZ) and hydrophobic clotrimazole (CTZ) MTZ and CTZ are antimicrobial agents that have a history of use to treat vaginal infections.

Figure 8A:
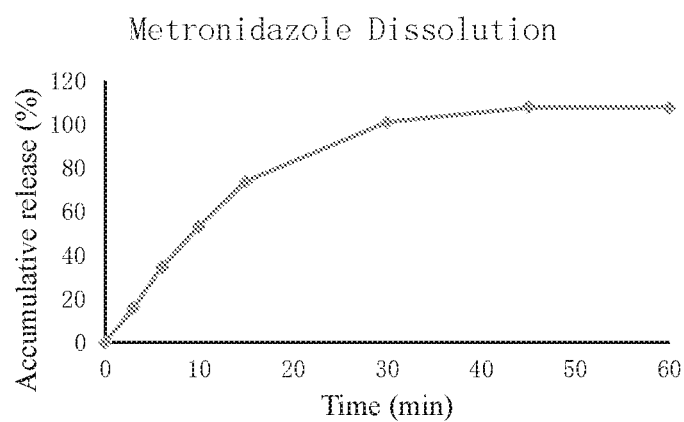
FIGS. 8A-8B show two release profiles of metronidazole (FIG. 8A) and clotrimazole (FIG. 8B) from one multilayer film. Polymer composition of the two layers of the film were utilized to release the two actives at two different rates.
Figure 8B:
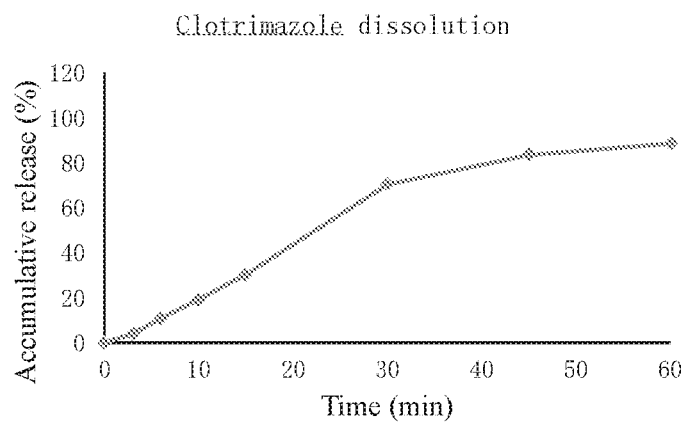

As described above, The MTZ/CTZ combination multilayer film was manufactured in a two-step process. All films were manufactured utilizing a twin-screw NANO 16 Leistritz extruder. The CTZ film composed of 33.75% (w/w) HPC, 33.75% (w/w) PEO N80 4.99% (w/w) PEG400, 2.5% vitamin E acetate, 25.00% (w/w) CTZ. The MTZ film composed of 45.00% (w/w) PEO N80, 26.25% (w/w) PEO N10, 2.25% (w/w) PEG400, 1.50% (w/w) vitamin E acetate, and 25% MTZ. The process used to develop the multilayer film required a sequential co-HME procedure. This process yielded a multilayer film containing one layer of the MTZ formulation and one layer containing the CTZ formulation. All films were off white, translucent, flexible and smooth. The multilayer film dissolution showed distinct release profiles for MTZ and CTZ (see FIG. 8).

What is claimed is:

1. A method of preparing a vaginal drug delivery film, comprising: extruding through a die a composition comprising one or more active pharmaceutical ingredients, from 45% to 60% by weight of a high molecular weight polyethylene oxide carrier having a molecular weight of from 100,000 to 700,000 Da, from 15% to 30% by weight of a medium molecular weight polyethylene oxide carrier having a molecular weight of from 3000 to 8000 Da, and from about 1% to about 4% of a low molecular weight polyethylene oxide having a molecular weight of from 200 to 600 Da, to thereby provide the film.

2. The method of claim 1, wherein the active pharmaceutical ingredient is a hydrophobic active.

3. The method of claim 1, wherein the active pharmaceutical ingredient is a hydrophilic active.

4. The method of claim 1, wherein the active pharmaceutical ingredient is a protein or peptide.

5. The method of claim 1, wherein the active pharmaceutical ingredient is a bacteria.

6. The method of claim 1, wherein the active pharmaceutical ingredient is an oligonucleotide or nucleotide.

7. The method of claim 1, wherein the active pharmaceutical ingredient is a polysaccharide or sugar.

8. The method of claim 1, wherein the active pharmaceutical ingredient is an antibiotic, antiviral, antifungal, steroid, cytotoxic, anti-proliferative, anti-inflammatory, analgesic, or diagnostic agent.

9. The method of claim 1, wherein the composition comprises two or more active pharmaceutical ingredients.

10. The method of claim 9, wherein the active pharmaceutical ingredients are an antibiotic and a probiotic.

11. The method of claim 9, wherein the active pharmaceutical ingredients are a contraceptive and an anti-HIV agent.

12. The method of claim 9, wherein the active pharmaceutical ingredients are two or more anti-HIV agents, anti-herpes agents, and/or anti-hepatitis C agents.

13. The method of claim 9, wherein the active pharmaceutical ingredients are dapivirine and levonorgestrel.

14. The method of claim 9, wherein the active pharmaceutical ingredients are metronidazole and *Lactobacillus*.

15. The method of claim 1, wherein the active pharmaceutical ingredient is dapivirine, metronidazole, griffithsin, levonorgestrel, *Lactobacillus*, or any combination thereof.

16. The method of claim 1, wherein the high molecular weight polyethylene oxide has a molecular weight of about 200,000 Da.

17. The method of claim 1, wherein the medium molecular weight polyethylene oxide has a molecular weight of about 4000 Da.

18. The method of claim 1, wherein the low molecular weight polyethylene oxide has a molecular weight of about 400 Da.

19. The method of claim 1, wherein the composition further comprises one or more of polymers selected from the group consisting of polyvinyl pyrrolidone, hydroxyethyl cellulose, hydroxypropyl cellulose, hydroxypropylmethyl cellulose, and combinations thereof.

20. The method of claim 1, wherein the composition further comprises from 0.1% to 5% by weight of one or more ingredients selected from the group consisting of a plasticizer, an antioxidant, and disintegration agent.

21. The method of claim 1, wherein the film is extruded through the die at a thickness of from 10 μm to 5 mm.

22. The method of claim 1, wherein the film has a water content of less than 10% by weight.

23. The method of claim 1, wherein the film is extruded at a temperature of from 40° C. to 250° C.

24. The method of claim 1, further comprising extruding a second composition comprising one or more active pharmaceutical ingredients and one or more polymer carriers at an elevated temperature through a die on top of the film.

* * * * *